(12) United States Patent
Iwahori et al.

(10) Patent No.: US 9,579,445 B2
(45) Date of Patent: Feb. 28, 2017

(54) DIALYSATE EXTRACTION APPARATUS

(71) Applicant: Nikkiso Company Limited, Tokyo (JP)

(72) Inventors: Tadashi Iwahori, Shizuoka (JP);
Hiroshi Nimura, Shizuoka (JP);
Hachiro Edamura, Shizuoka (JP);
Masahiro Takahashi, Shizuoka (JP)

(73) Assignee: NIKKISO COMPANY LIMITED, Tokyo (JP)

( * ) Notice: Subject to any disclaimer, the term of this patent is extended or adjusted under 35 U.S.C. 154(b) by 353 days.

(21) Appl. No.: 14/163,051

(22) Filed: Jan. 24, 2014

(65) Prior Publication Data

US 2014/0138301 A1 May 22, 2014

Related U.S. Application Data

(63) Continuation of application No. PCT/JP2012/068983, filed on Jul. 26, 2012.

(30) Foreign Application Priority Data

Jul. 27, 2011 (JP) .................................. 2011-164854

(51) Int. Cl.
*A61M 1/36* (2006.01)
*B01D 35/147* (2006.01)
(Continued)

(52) U.S. Cl.
CPC .......... *A61M 1/3643* (2013.01); *A61M 1/168* (2013.01); *A61M 39/10* (2013.01);
(Continued)

(58) Field of Classification Search
CPC .... A61M 39/10; A61M 1/3643; A61M 39/16; A61M 39/20; A61M 1/168; B01D 35/147; B01D 35/153; Y10T 137/9029
See application file for complete search history.

(56) References Cited

FOREIGN PATENT DOCUMENTS

| JP | 2003-093501 | 4/2003 |
|---|---|---|
| JP | 2004-313522 | 11/2004 |

(Continued)

OTHER PUBLICATIONS

English translation of Japanese Patent Application No. 2009-207706 A (Sep. 2009).*

(Continued)

*Primary Examiner* — John Kim
(74) *Attorney, Agent, or Firm* — The Dobrusin Law Firm, P.C.

(57) ABSTRACT

A dialysate extraction apparatus which can reliably perform cleaning and disinfecting on an inside of a collection port without extending a separate flow route from an on-off device. The dialysate extraction apparatus includes a dialysate extraction device having an inlet and an outlet which can circulate a liquid, and having a collection port which can collect the circulating liquid; and a cap which is attachable to and detachable from the collection port of the dialysate extraction device and which can turn on and off the collection port. When the cap is attached, the collection port defines a guide route which guides the liquid introduced from the inlet to a tip a side of the collection port, and a discharge route which discharges the liquid guided by the guide route to the outlet side.

17 Claims, 17 Drawing Sheets

(51) Int. Cl.
*A61M 1/16* (2006.01)
*B01D 35/153* (2006.01)
*A61M 39/10* (2006.01)
*A61M 39/16* (2006.01)
*A61M 39/20* (2006.01)

(52) U.S. Cl.
CPC ............ *A61M 39/16* (2013.01); *A61M 39/20* (2013.01); *B01D 35/147* (2013.01); *B01D 35/153* (2013.01); *Y10T 137/9029* (2015.04)

(56) References Cited

FOREIGN PATENT DOCUMENTS

JP    2009-207706        9/2009
WO   2009/074588 A1    6/2009

OTHER PUBLICATIONS

Supplementary European Search Report dated Feb. 18, 2015 for application PCT/JP2012068983.

* cited by examiner

DIALYSATE EXTRACTION APPARATUS

FIELD

The present invention relates to a dialysate extraction apparatus including a dialysate extraction device having an inlet and an outlet which are connected to a flow route of a liquid and which can circulate the liquid and having a collection port which can collect the circulating liquid; and an on-off device which is attachable to and detachable from the collection port of the dialysate extraction device and which can turn on and off the collection port.

BACKGROUND

In recent years, in a dialysis apparatus as a blood purification apparatus, a technology has been proposed in which priming, returning blood and substitution (emergency infusion) are performed by using a dialysate to be supplied to a dialyzer during dialysis treatment (in particular, online HDF or online HF), or a technology has been proposed in which the dialysate is used as a substitution solution for the online HDF or the online HF. For example, PTL 1 discloses a dialysis apparatus including a substitution line where one end is connected to a dialysate extraction port (collection port) formed in a predetermined section of a dialysate introduction line and the other end is connected to a blood circuit (artery side blood circuit or vein side blood circuit); and a substitution pump which is arranged in the substitution line. In order for such a dialysis apparatus to perform the priming, the returning blood or the substitution (emergency infusion), the substitution pump is driven to supply the dialysate in the dialysate introduction line to the blood circuit (artery side blood circuit or vein side blood circuit).

In general, a cap (on-off device) is attachable to and detachable from the dialysate extraction port, and the substitution line is connected by detaching the cap and when the substitution line is not connected, the dialysate flowing in the dialysate introduction line is not caused to leak out by attaching the cap. For example, in order to clean and disinfect a pipe for circulating the dialysate, such as the dialysate introduction line and the dialysate discharge line, cleaning water or disinfecting solution is circulated in the pipe in a state where the cap is attached to the collection port. In this manner, the cleaning water or the disinfecting solution is prevented from leaking out.

Thus, if the cap comes into close contact with and seals an inner peripheral surface of the collection port, the cleaning water or the disinfecting solution cannot be circulated with respect to the sealed portion, thereby creating a possibility that the cleaning and the disinfecting may be insufficiently performed. Therefore, in the related art, in order that the cap seals an outer peripheral surface of the collection port, a configuration has been proposed where the cleaning water or the disinfecting solution can reach the inner peripheral surface of the collection port (for example, refer to PTL 2 and PTL 3). Thus, if a flow route is extended to circulate the cleaning water or the disinfecting solution from the cap, the cleaning water or the disinfecting solution is circulated inside the collection port, thereby enabling the cleaning and the disinfecting to be sufficiently performed. Some examples may be found in PTL 1: Japanese Unexamined Patent Application Publication No. 2004-313522; PTL 2: Japanese Unexamined Patent Application Publication No. 2003-93501; and PTL 3: Japanese Unexamined Patent Application Publication No. 2009-207706 all of which are expressly incorporated by reference herein for all purposes.

SUMMARY

However, in the dialysate extraction apparatus in the related art, there has been a problem in that the cleaning water or the disinfecting solution is unlikely to reach the inside of the collection port unless the flow route is extended to circulate the cleaning water or the disinfecting solution from the cap (on-off device). That is, even if the cap is adopted simply to seal the outer peripheral surface of the collection port, a single closed space is only formed inside the collection port. Thus, a liquid flowing in the dialysate introduction line is hardly circulated to the inside of the collection port. Accordingly, it is necessary to form a separate flow route extended from the cap in order to circulate the liquid. When the separate flow route is extended, another layout is newly required for the flow route and in addition, there is a problem in that maintenance is troublesome.

The present invention is made in view of such circumstances, and aims to provide a dialysate extraction apparatus which can reliably perform cleaning and disinfecting on an inside of a collection port without extending a separate flow route from an on-off device.

According to the invention described herein, there is provided a dialysate extraction apparatus including a dialysate extraction device having an inlet and an outlet which are connected to a flow route of a liquid and which can circulate the liquid, and having a collection port which can collect the circulating liquid; and an on-off device which is attachable to and detachable from the collection port of the dialysate extraction device and which can turn on and off the collection port. In a state where the on-off device is attached, the collection port defines a guide route which guides the liquid introduced from the inlet to a tip side of the collection port, and a discharge route which discharges the liquid guided by the guide route to the outlet side.

According to the invention described herein, and in the dialysate extraction apparatus described herein, the dialysate extraction device has a cylindrical outer peripheral wall which covers an outer periphery of the collection port, and the on-off device includes a sealing device which seals between the on-off device and an outer peripheral surface of the outer peripheral wall or between the on-off device and a tip surface.

According to the invention described herein, and in the dialysate extraction apparatus described herein, the inside of the collection port serves as the guide route, and a section between an outer peripheral surface of the collection port and an inner peripheral surface of the outer peripheral wall serves as the discharge route.

According to the invention described herein, and in the dialysate extraction apparatus described herein, the outer peripheral wall is formed to protrude by covering the tip of the collection port.

According to the invention described herein, and in the dialysate extraction apparatus described herein, the collection port can be connected to a connection line for circulating an extracted liquid via a connection device, and the connection line can be connected to the collection port by fitting the inner peripheral surface of the connection device into the outer peripheral surface of the collection port and by engaging the outer peripheral surface of the connection device with the inner peripheral surface of the outer peripheral wall.

According to the invention described herein, and in the dialysate extraction apparatus described herein, in a state where the connection device is connected to the collection port, the liquid is blocked so as not to flow out via the discharge route.

According to the invention described herein, and in the dialysate extraction apparatus described herein, the dialysate extraction device includes a pressure difference forming device which increases a pressure of a liquid flowing toward the guide route as compared to a pressure of a liquid flowing toward the outlet out of the liquids introduced from the inlet.

According to the invention described herein, and the dialysate extraction apparatus described herein, the pressure difference forming device and the collection port are formed from an integral part.

According to the invention described herein, and in the dialysate extraction apparatus described herein, the pressure difference forming device is formed to have a circulation route of the liquid flowing from the inlet toward the collection port, and the circulation route has a tapered surface in which a diameter of the flow route gradually decreases toward the collection port.

According to the invention described herein, and in the dialysate extraction apparatus described herein, the pressure difference forming device is formed to have an orifice or a venturi shape for decreasing a pressure by squeezing liquid flow from the inlet toward the outlet.

According to the invention described herein, and in the dialysate extraction apparatus described herein, the dialysate extraction device includes a check valve which allows the liquid to flow out from the collection port and blocks the liquid not to flow in from outside via the collection port.

According to the invention described herein, and in the dialysate extraction apparatus described herein, the inlet and the collection port are formed on substantially the same straight line.

According to the invention described herein, there is provided a blood purification apparatus including the dialysate extraction apparatus herein.

According to the invention described herein, and in a state where the on-off device is attached, the collection port defines the guide route which guides the liquid introduced from the inlet to the tip side of the collection port, and the discharge route which discharges the liquid guided by the guide route to the outlet side. Therefore, it is possible to circulate cleaning water or disinfecting solution via the guide route and the discharge route, and thus it is possible to reliably perform the cleaning and the disinfecting on the inside of the collection port without extending a separate flow route from the on-off device. Furthermore, in addition to a function of collecting the liquid, the collection port also has a function of defining the guide route and the discharge route. Therefore, a configuration can be simplified by eliminating a need to provide a separate defining device.

According to the invention described herein, and the dialysate extraction device has the cylindrical outer peripheral wall which covers the outer periphery of the collection port, and the on-off device includes the sealing device which seals between the on-off device and the outer peripheral surface of the outer peripheral wall or between the on-off device and a tip surface. Therefore, in the state where the on-off device is attached to the collection port, it is possible to more reliably define the guide route and the discharge route, and it is possible to more excellently circulate the cleaning water or the disinfecting solution.

According to the invention described herein, and the inside of the collection port serves as the guide route, and the section between the outer peripheral surface of the collection port and the inner peripheral surface of the outer peripheral wall serves as the discharge route. Therefore, it is possible to more smoothly and excellently circulate the cleaning water or the disinfecting solution via the guide route and the discharge route.

According to the invention described herein, and the outer peripheral wall is formed to protrude by covering the tip of the collection port. Therefore, even in a state where the on-off device is detached from the collection port, it is possible to avoid a case where a human finger may touch the collection port, and thus it is possible to achieve more reliable hygiene management.

According to the invention described herein, and the connection line can be connected to the collection port by fitting the inner peripheral surface of the connection device into the outer peripheral surface of the collection port and by engaging the outer peripheral surface of the connection device with the inner peripheral surface of the outer peripheral wall. Therefore, a connection surface of the connection device with respect to the collection port corresponds to the inner peripheral surface. Accordingly, it is possible to avoid a case where a human finger may touch the connection surface with respect to the collection port before the connection, and thus it is possible to achieve more reliable hygiene management.

According to the invention described herein, and in the state where the connection device is connected to the collection port, the liquid is blocked so as not to flow out via the discharge route. Therefore, when collecting the liquid through the collection port via the connection device, it is possible to reliably avoid the case where the liquid may flow out from the discharge route, and thus it is possible to more excellently circulate the collected liquid with respect to the connection line.

According to the invention described herein, the dialysate extraction device includes the pressure difference forming device which increases the pressure of the liquid flowing toward the guide route as compared to the pressure of the liquid flowing toward the outlet out of the liquids introduced from the inlet. Therefore, it is possible to reliably circulate the cleaning water or the disinfecting solution with respect to the guide route and the discharge route using a pressure difference generated by the pressure difference forming device.

According to the invention described herein, the pressure difference forming device and the collection port are formed from the integral part. Therefore, it is possible to reduce the number of parts in the dialysate extraction device, and thus it is possible to save manufacturing costs and maintenance costs.

According to the invention described herein, the pressure difference forming device is formed to have the circulation route of the liquid flowing from the inlet toward the collection port, and the circulation route has the tapered surface in which the diameter of the flow route gradually decreases toward the collection port. Therefore, it is possible to relatively increase the pressure of the liquid flowing from the inlet toward the guide route as compared to the pressure of the liquid flowing from the inlet toward the discharge port, and thus it is possible to reliably circulate the cleaning water or the disinfecting solution with respect to the guide route and the discharge route.

According to the invention described herein, the pressure difference forming device is formed to have the orifice or the venturi shape for decreasing the pressure by squeezing the liquid flow from the inlet toward the outlet. Therefore, it is possible to relatively decrease the pressure of the liquid flowing from the inlet toward the guide route as compared to the pressure of the liquid flowing from the inlet toward the discharge port, and thus it is possible to reliably circulate the cleaning water or the disinfecting solution with respect to the guide route and the discharge route.

According to the invention described herein, the dialysate extraction device includes the check valve which allows the liquid to flow out from the collection port and blocks the liquid not to flow in from outside via the collection port. Therefore, for example when connecting the connection line to the collection port, it is possible to avoid the case where the liquid inside the flow route such as the connection line may flow in from the collection port.

According to the invention described herein, the inlet and the collection port are formed on substantially the same straight line. Therefore, the liquid introduced from the inlet flows toward the collection port as it is. Accordingly, it is possible to more reliably and excellently circulate the cleaning water or the disinfecting solution via the guide route and the discharge route, and thus it is possible to more reliably perform the cleaning and the disinfecting on the inside of the collection port.

According to the invention described herein, a blood purification apparatus can be provided which can circulate the cleaning water or the disinfecting solution via the guide route and the discharge route and which can reliably perform the cleaning and the disinfecting on the inside of the collection port without extending the separate flow route from the on-off device. Furthermore, in addition to the function of collecting the liquid, the collection port also has the function of defining the guide route and the discharge route. Therefore, the blood purification apparatus can be provided in which the configuration can be simplified by eliminating the need to provide the separate defining device.

DETAILED DESCRIPTION

Hereinafter, an embodiment of the present invention will be described in detail with reference to the drawings.

Figure 1:
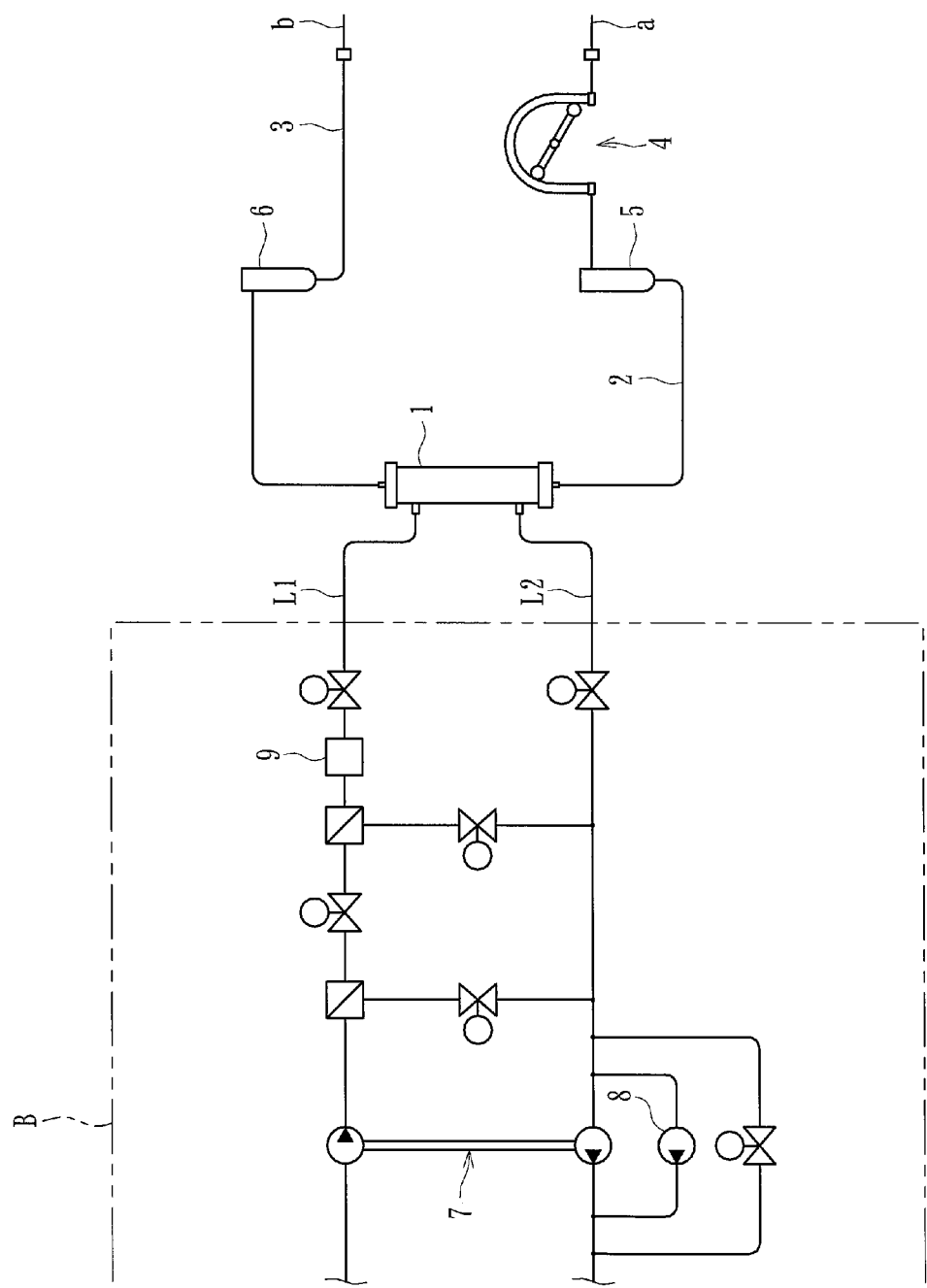
FIG. 1 is a schematic view illustrating a blood purification apparatus which adopts a dialysate extraction apparatus of the present invention.
Figure 2:
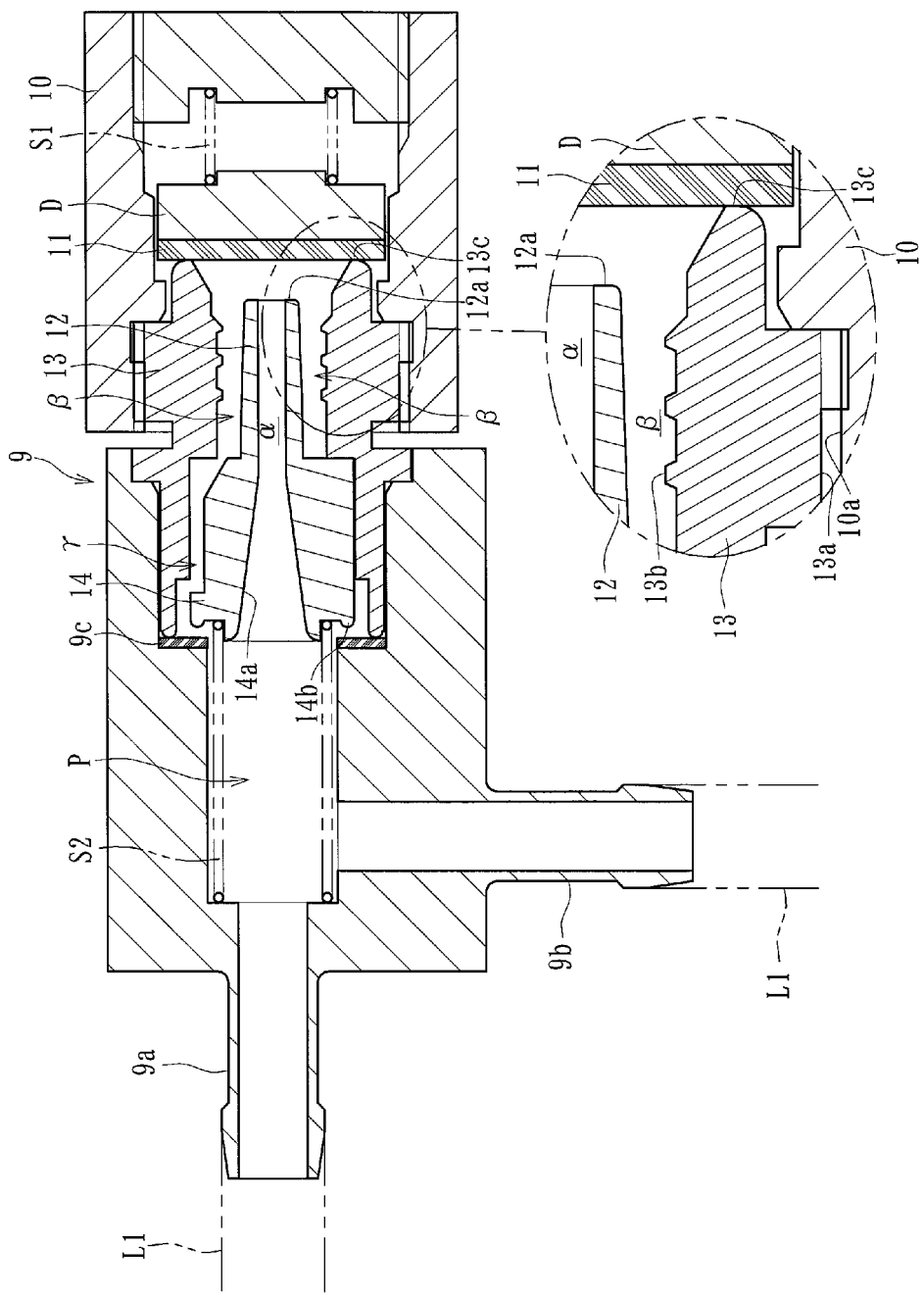
FIG. 2 is a schematic cross-sectional view illustrating a dialysate extraction apparatus (state where an on-off device is attached to a collection port) according to a first embodiment of the present invention.

A dialysate extraction apparatus according to the present embodiment is arranged in a blood purification apparatus for use in blood purification treatment (hemodialysis treatment), and enables a dialysate to be collected. As illustrated in FIG. 1, the blood purification apparatus adopting the dialysate extraction apparatus is mainly configured to include a blood circuit in which an artery side blood circuit 2 and a vein side blood circuit 3 are connected to a dialyzer 1 (blood purifier); and a dialysis device B which has a dialysate introduction line L1 and a dialysate discharge line L2.

The dialyzer 1 is to purify blood and is connected to the artery side blood circuit 2 and the vein side blood circuit 3 respectively which configure the blood circuit. The dialyzer 1 is connected to the dialysate introduction line L1 and the dialysate discharge line L2 respectively. Patient's blood collected through an artery side puncture needle a is extracorporeally circulated in the blood circuit, and the dialyzer 1 performs blood purification and ultrafiltration to return the blood to the patient through a vein side puncture needle b. Reference numerals 5 and 6 illustrate air trap chambers.

In addition, a duplex pump 7 which supplies the dialysate prepared to have a predetermined concentration to the dialyzer 1 and discharges the dialysate from the dialyzer 1 is connected to the dialysate introduction line L1 and the dialysate discharge line L2. Further, a plurality of bypass lines and electromagnetic valves are arranged in optional positions inside the dialysis device B. An ultrafiltration pump 8 is connected to the bypass line which bypasses the duplex pump 7.

Then, in order to disinfect or clean a pipe inside the dialysis device B, tips of the dialysate introduction line L1 and the dialysate discharge line L2 are detached from the dialyzer 1, and the pipe is caused to short-circuit by connecting the tips to each other using a coupler for example. Thereafter, disinfecting solution (hot water or disinfecting chemical) or cleaning water (clean water) is introduced from outside of the dialysis device B (for example, dialysate supplying device), and a liquid (dialysate or the like) inside the pipe in the dialysis device B is substituted. For example, the disinfecting solution may be introduced into the pipe from the inside of a tank for substitution by branching a flow route from the dialysate discharge line L2 and by inserting the tip to the tank containing the dialysate.

Here, a dialysate extraction apparatus according to a first embodiment of the present invention is connected to the dialysate introduction line L1. As illustrated in FIGS. 2 to 6, the dialysate extraction apparatus according to the present embodiment includes an inlet 9a and an outlet 9b which are connected to the dialysate introduction line L1 (flow route of a liquid) and which can circulate the liquid (dialysate); a dialysate extraction device 9 having a collection port 12 which can collect the circulating liquid; and a cap 10 serving as an on-off device which is attachable to and detachable from the collection port 12 of the dialysate extraction device 9 and which can turn on and off the collection port 12.

More specifically, in the dialysate extraction device 9, the dialysate introduction line L1 is connected to the inlet 9a and outlet 9b respectively, and the inside thereof enables the dialysate to be circulated. The flow route (flow route through which the dialysate flows from the inlet 9a to the outlet 9b) extends in an L-shape bent by approximately 90 degrees at a branch portion P. The collection port 12 is formed to be positioned on substantially the same straight line with respect to the inlet 9a.

Furthermore, the dialysate extraction device 9 has a cylindrical outer peripheral wall 13 which covers an outer periphery of the collection port 12. In the outer peripheral wall 13, an outer peripheral surface thereof has a screw portion 13a which can be screwed to a screw portion 10a of the cap 10 (on-off device) and an inner peripheral surface thereof has a screw portion 13b which can be screwed to a screw portion 15ba of a connection device 15 (refer to FIGS. 5 and 6), respectively. That is, the collection port 12 can be connected to a connection line L3 via the connection device 15 by engaging the connection device 15 with the outer peripheral wall 13 for fixing.

Furthermore, the outer peripheral wall 13 according to the present embodiment is formed to protrude by covering a tip 12a of the collection port 12. That is, a protruding dimension of the outer peripheral wall 13 is set to be larger than a protruding dimension of the collection port 12. Accordingly, the tip 12a of the collection port 12 is covered with the outer peripheral wall 13. In this manner, even when the cap 10 is detached from the collection port 12, it is possible to avoid a case where a human finger may touch the collection port 12, and thus it is possible to achieve more reliable hygiene management.

Figure 5:
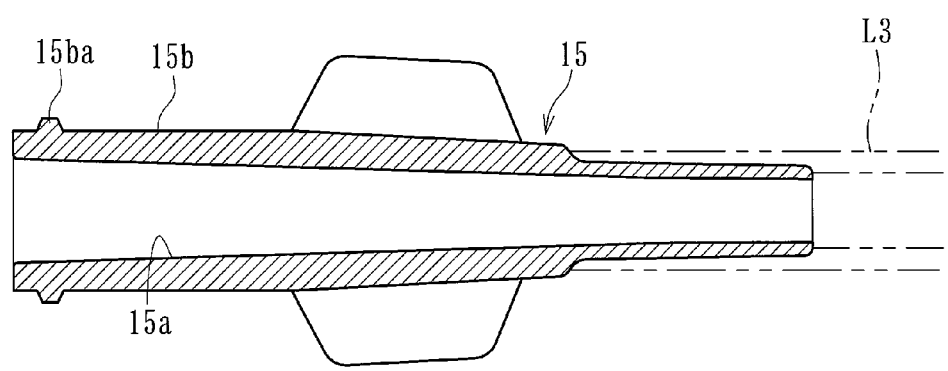
FIG. 5 is a schematic cross-sectional view illustrating a connection device which can be connected to a collection port of the dialysate extraction apparatus.
Figure 6:
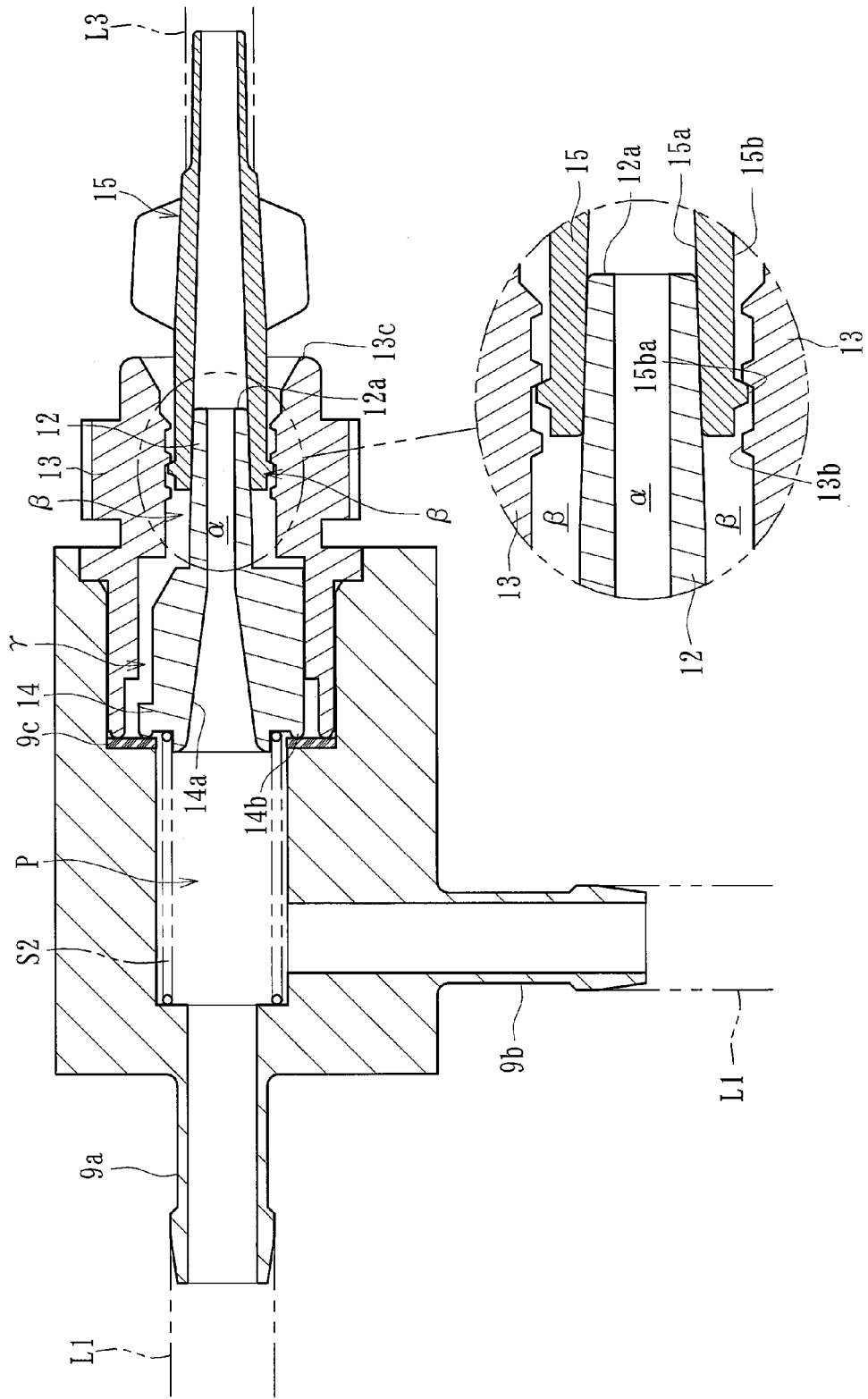
FIG. 6 is a schematic cross-sectional view illustrating a dialysate extraction device (state where an on-off device is detached and state where a connection device is connected) in the dialysate extraction apparatus.

As illustrated in FIG. 5, the connection device 15 is attached to a tip portion of the connection line L3 which circulates the liquid collected through the collection port 12, and is formed from a substantially cylindrical member having an inner peripheral surface 15a and an outer peripheral surface 15b. The screw portion 15ba which can be screwed to the screw portion 13b of the outer peripheral wall 13 is integrally formed in the tip side (portion side to be connected to the collection port 12) of the outer peripheral surface 15b. Then, as illustrated in FIG. 6, the inner peripheral surface 15a of the connection device 15 is fitted to the outer peripheral surface of the collection port 12, and the screw portion 15ba of the outer peripheral surface 15b of the connection device 15 is screwed to and locked in the screw portion 13b formed on the inner peripheral surface of the outer peripheral wall 13. In this manner, the connection line L3 can be connected to the collection port 12.

For example, the connection line L3 according to the present embodiment is connected to an air trap chamber 5 connected to the artery side blood circuit 2, or is connected to an air trap chamber 6 connected to the vein side blood circuit 3. The connection line L3 can supply the dialysate in the dialysate introduction line L1 to the artery side blood circuit 2 or the vein side blood circuit 3. In this manner, it is possible to perform priming, substitution or returning blood by using the dialysate, or alternatively it is possible to use the dialysate as a substitution solution for online HDF treatment or online HF treatment.

In this manner, the inner peripheral surface 15a of the connection device 15 is fitted to the outer peripheral surface of the collection port 12, the outer peripheral surface 15b of the connection device 15 is locked in the inner peripheral surface of the outer peripheral wall 13, and thus the connection line L3 can be connected to the collection port 12. Accordingly, a connection surface of the connection device 15 with respect to the collection port 12 corresponds to the inner peripheral surface (inside of the connection device 15). Therefore, it is possible to avoid a case where a human finger may touch the collection port 12, and thus it is possible to achieve more reliable hygiene management.

Figure 3:
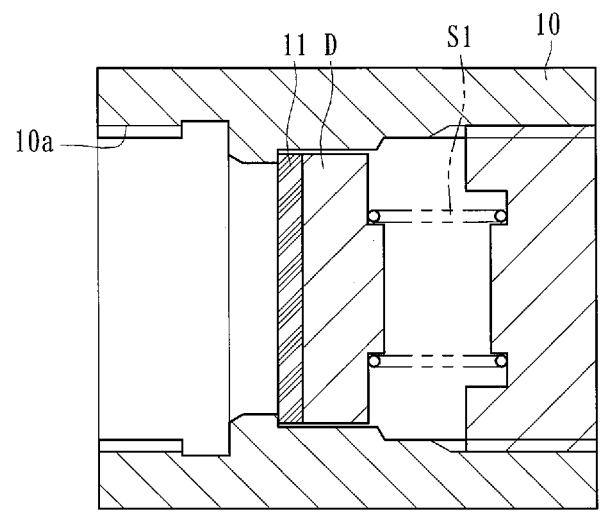
FIG. 3 is a schematic cross-sectional view illustrating a cap (on-off device) in the dialysate extraction apparatus.
Figure 4:
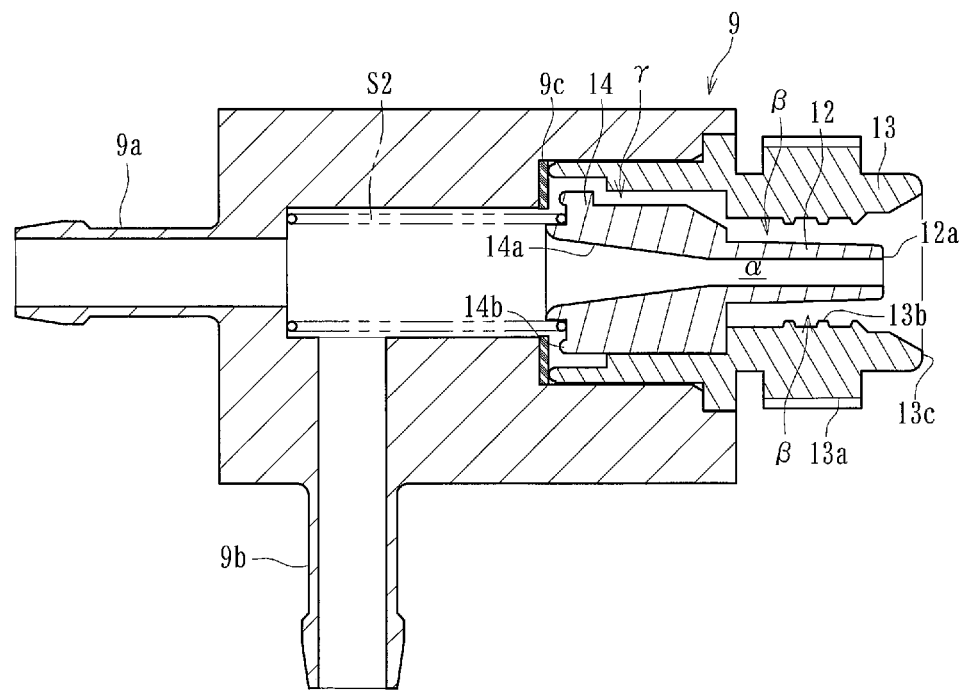
FIG. 4 is a schematic cross-sectional view illustrating a dialysate extraction device (state where an on-off device is detached) in the dialysate extraction apparatus.

The cap 10 serving as an on-off device can be attached to the outer peripheral wall 13 by the screw portion 10a formed on the inner peripheral surface being screwed to the screw portion 13a of the outer peripheral wall 13. As illustrated in FIG. 3, the cap 10 according to the present embodiment includes a sealing device 11 which seals between the cap 10 and a tip surface 13c of the outer peripheral wall 13. The sealing device 11 is attached to one surface of an attachment member D, and is always biased against the tip surface 13c side (collection port 12 side) of the outer peripheral wall 13, together with the attachment member D by a spring S1, thereby enabling the sealing to be more reliably performed.

Here, the collection port 12 of the dialysate extraction device 9 according to the present embodiment is configured to define a guide route α which guides the liquid introduced from the inlet 9a into the collection port 12; and a discharge route β which discharges the liquid guided by the guide route α to the outlet 9b side, in a state where the cap 10 is attached. That is, if the cap 10 is screwed and attached to the outer peripheral wall 13, the sealing device 11 seals the tip surface 13c of the outer peripheral wall 13 to form a sealed surface. The sealed surface is defined by the guide route α and the discharge route β in the collection port 12. Then, the inside of the collection port 12 serves as the guide route α, and a portion between the outer peripheral surface of the collection port 12 and the inner peripheral surface of the outer peripheral wall 13 serves as the discharge route β.

In this manner, the collection port 12 according to the present embodiment has not only a function of collecting the liquid by being connected to the connection device 15 but also a function of defining the guide route α and the discharge route β in a state where the cap 10 is attached. In the present embodiment, the collection port 12 is configured to have the cylindrical member, but if a tubular member is used which can define the guide route α and the discharge route β, any member having other shapes (for example, those having a rectangular cross-section) may be used.

On the other hand, the dialysate extraction device 9 has a connection route γ for connecting the discharge route β and a flow route of the branch portion P side. In this manner, the liquid flowing from the Inlet 9a toward the tip of collection port 12 via the branch portion P and the guide route α can be discharged from the outlet 9b through the discharge route β and the connection route γ, and can flow out from the outlet 9b by merging with the liquid flowing from the inlet 9a toward the outlet 9b via the branch portion P.

Furthermore, the dialysate extraction device 9 according to the present embodiment includes a pressure difference forming device 14 which increases a pressure of the liquid flowing toward the guide route α as compared to the pressure of the liquid flowing toward the outlet 9b out of the liquids introduced from inlet 9a. The pressure difference forming device 14 is arranged near the branch portion P of the dialysate extraction device 9, and is formed to have a circulation route 14a of the liquid flowing from the inlet 9a toward the collection port 12. The circulation route 14a is formed from a tapered surface in which a diameter of the flow route gradually decreases toward the collection port 12 side (right side in FIG. 2). In this manner, it is possible to relatively increase the pressure of the liquid flowing from the inlet 9a toward the collection port 12 as compared to the pressure of the liquid flowing from the inlet 9a toward the outlet 9b.

In addition, the pressure difference forming device 14 and the collection port 12 according to the present embodiment are formed from an integral part (for example, integrally molded part). In this manner, if the pressure difference forming device 14 and the collection port 12 are formed from the integral part, it is possible to reduce the number of parts in the dialysate extraction device 9, and thus it is possible to save manufacturing costs and maintenance costs. The pressure difference forming device 14 and the collection port 12 may be separately formed and connected to each other so as to be the integral part.

Furthermore, a to-be-sealed portion 14b is formed at a portion opposing the sealing member 9c in the pressure difference forming device 14. The pressure difference forming device 14 and the collection port 12 are always biased against the sealing member 9c by a spring S2 in a direction in which the to-be-sealed portion 14b is separated. Then, when the connection device 15 is connected to the collection port 12 (that is, during a process where the screw portion 15ba of the outer peripheral surface 15b of the connection device 15 is screwed to the screw portion 13b formed on the inner peripheral surface of the outer peripheral wall 13), the pressure difference forming device 14 and the collection port 12 are moved against a biasing force of the spring S2, and the to-be-sealed portion 14b comes into contact with and seals the sealing member 9c, thereby enabling the connection route γ to be blocked.

Then, in a state where the connection device 15 is connected to the collection port 12, the liquid is blocked so as not to flow out via the discharge route β. In this manner, in the state where the connection device 15 is connected to the collection port 12, the liquid is blocked so as not to flow out via the discharge route β. Therefore, when collecting the liquid from the collection port 12 via the connection device 15, it is possible to reliably avoid a case where the liquid leaks out from the discharge route β, and thus it is possible to excellently circulate the collected liquid with respect to the connection line L3.

According to the first embodiment, in a state where the cap 10 (on-off device) is attached, the collection port 12 defines the guide route α which guides the liquid introduced from the inlet 9a to the tip 12a of the collection port 12; and the discharge route β which discharges the liquid guided by the guide route α to the outlet 9b side. Therefore, it is possible to circulate the cleaning water or the disinfecting solution via the guide route α and the discharge route β, and thus it is possible to reliably perform the cleaning and the disinfecting on the inside of the collection port 12 without extending the separate flow route from the cap 10. Furthermore, in addition to the function of collecting the liquid, the collection port 12 also has the function of defining the guide route α and the discharge route β. Therefore, the configuration can be simplified by eliminating the need to provide a separate defining device.

In addition, the dialysate extraction device 9 has the cylindrical outer peripheral wall 13 which covers the outer periphery of the collection port 12, and the cap 10 includes the sealing device 11 which seals between the dialysate extraction device 9 and the tip surface 13c of the outer peripheral wall 13. Therefore, in a state where the cap 10 is attached to the collection port 12, it is possible to more reliably define the guide route α and the discharge route β, and thus it is possible to more excellently circulate the cleaning water or the disinfecting solution.

Furthermore, the inside of the collection port 12 serves as the guide route α, and the portion between the outer peripheral surface of the collection port 12 and the inner peripheral surface of the outer peripheral wall 13 serves as the discharge route β. Therefore, it is possible to more smoothly and excellently circulate the cleaning water or the disinfecting solution via the guide route α and the discharge route β. Furthermore, the dialysate extraction device 9 includes the pressure difference forming device 14 which increases the pressure of the liquid flowing toward the guide route α as compared to the pressure of the liquid flowing toward the outlet 9b out of the liquids introduced from the inlet 9a. Therefore, it is possible to more reliably circulate the cleaning water or the disinfecting solution with respect to the guide route α and the discharge route β by using a pressure difference formed by the pressure difference forming device 14.

In addition, the pressure difference forming device 14 is formed to have the circulation route 14a of the liquid flowing from the inlet 9a toward the collection port 12, and the circulation route 14a is formed from the tapered surface in which the diameter of the flow route gradually decreases toward the collection port 12 side. Therefore, it is possible to relatively increase the pressure of the liquid flowing from the inlet 9a toward the guide route α as compared to the pressure of the liquid flowing from the inlet 9a toward the outlet 9b, and thus it is possible to reliably circulate the cleaning water or the disinfecting solution with respect to the guide route α and the discharge route β.

In addition, according to the present embodiment, the inlet 9a and the collection port 12 are formed on substantially the same straight line. Therefore, the liquid introduced from the inlet 9a flows toward the collection port 12 as it is. Consequently, it is possible to more reliably and excellently circulate the cleaning water or the disinfecting solution via the guide route α and the discharge route β, and thus it is possible to more reliably perform the cleaning and the disinfecting on the inside of the collection port 12.

Next, a dialysate extraction apparatus according to a second embodiment of the present invention will be described.

Figure 7:
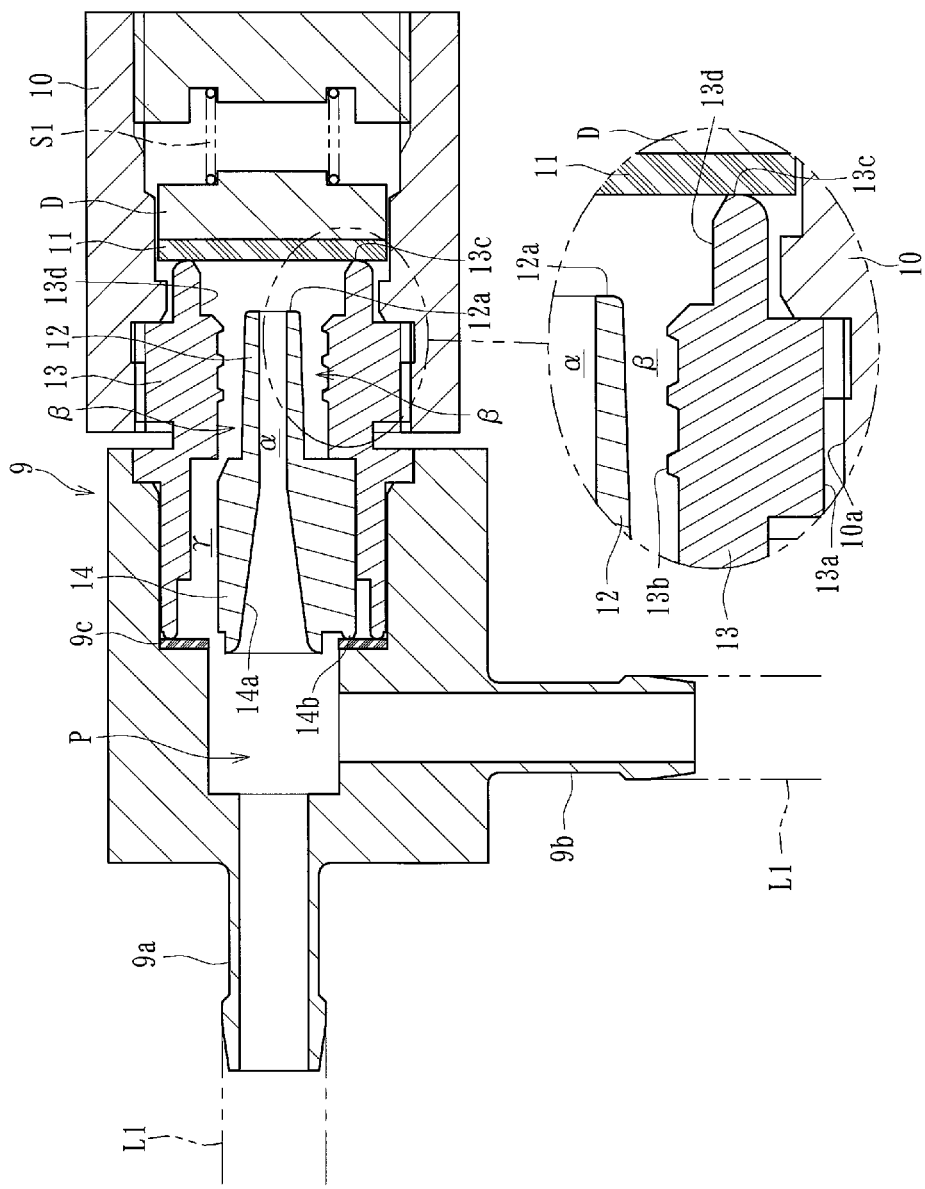
FIG. 7 is a schematic cross-sectional view of a dialysate extraction apparatus (state where an on-off device is attached to a collection port) according to a second embodiment of the present invention.
Figure 8:
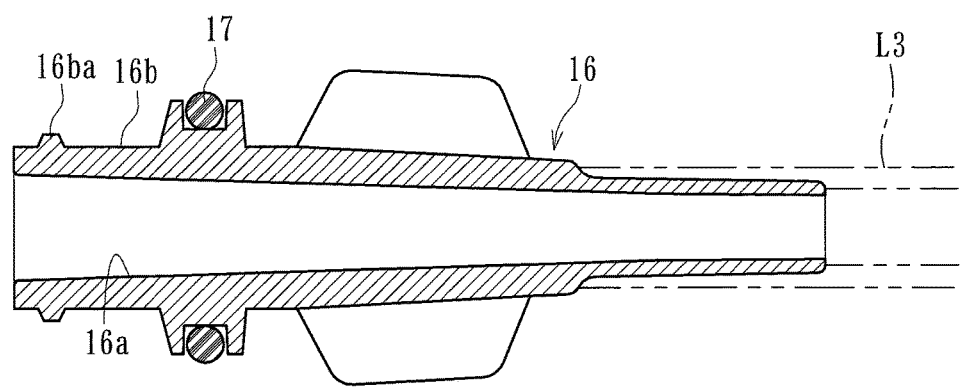
FIG. 8 is a schematic cross-sectional view illustrating a connection device which can be connected to a collection port of the dialysate extraction apparatus.
Figure 9:
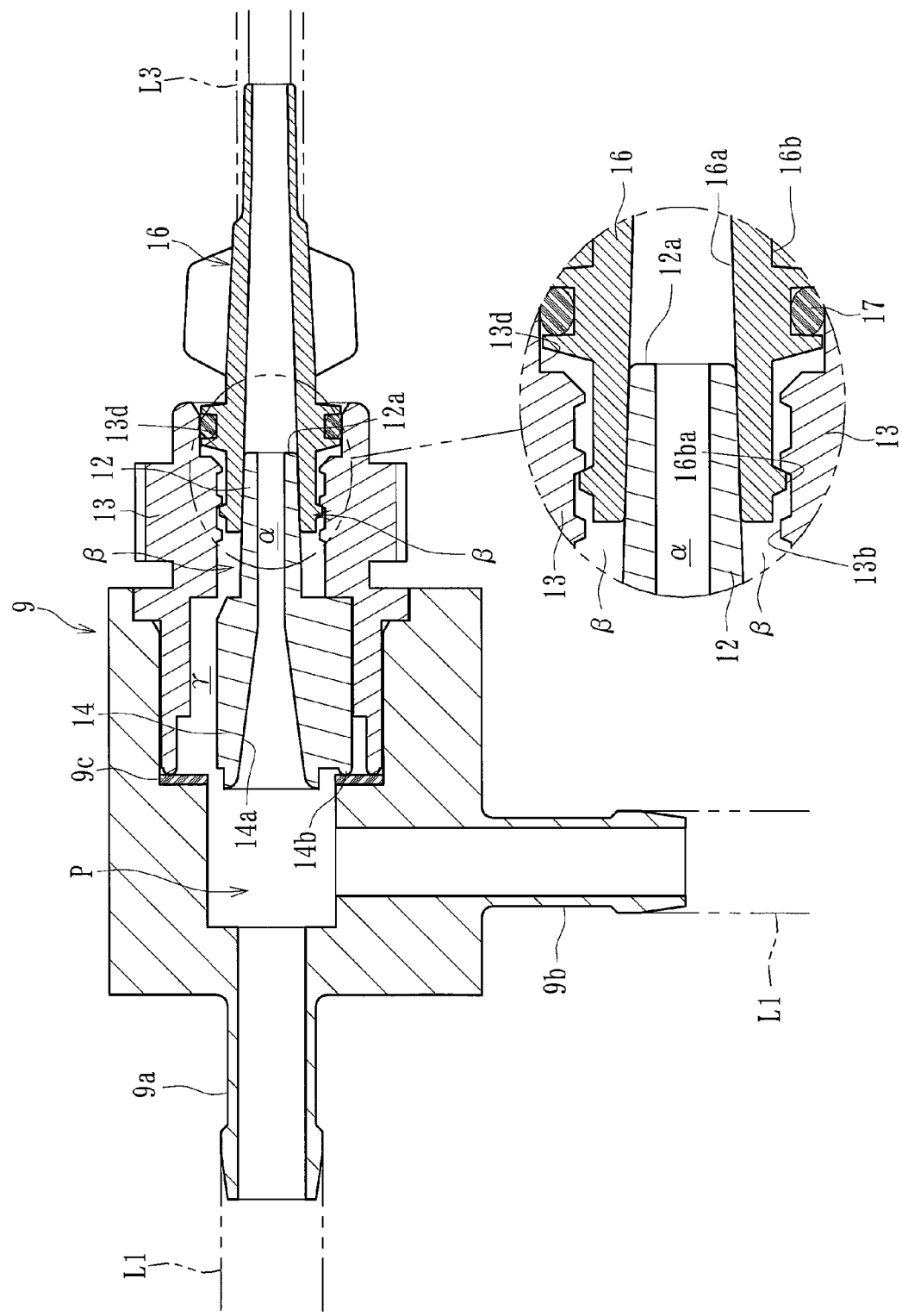
FIG. 9 is a schematic cross-sectional view illustrating a dialysate extraction device (state where an on-off device is detached and state where a connection device is connected) in the dialysate extraction apparatus.

Similar to the first embodiment, the dialysate extraction apparatus according to the present embodiment is connected to the dialysate introduction line L1 of the blood purification apparatus as illustrated in FIG. 1. As illustrated in FIGS. 7 to 9, the dialysate extraction apparatus includes the inlet 9a and the outlet 9b which are connected to the dialysate introduction line L1 (flow route of a liquid) and which can circulate the liquid (dialysate); the dialysate extraction device 9 having the collection port 12 which can collect the circulating liquid; and the cap 10 serving as the on-off device which is attachable to and detachable from the collection port 12 of the dialysate extraction device 9 and which can turn on and off the collection port 12. The same reference numerals are given to the configuring parts which are the same as those of the first embodiment, and detailed description thereof will not be repeated.

Similar to the first embodiment, the pressure difference forming device 14 and the collection port 12 are formed from the integral part (for example, integrally molded part), but are fixed inside the dialysate extraction device 9 unlike the first embodiment. That is, in the present embodiment, a sealing member 17 seals between the collection port 12 and a connection device 16 (refer to FIG. 8), and the liquid is not allowed to be circulated in the connection route γ.

As illustrated in FIG. 8, the connection device 16 is attached to a tip portion of the connection line L3 for circulating the liquid collected through the collection port 12, and is formed from a substantially cylindrical member having an inner peripheral surface 16a and an outer peripheral surface 16b. A screw portion 16ba which can be screwed to the screw portion 13b of the outer peripheral wall 13 is integrally formed in the tip side (portion side to be connected to the collection port 12) of the outer peripheral surface 16b. Then, as illustrated in FIG. 9, the inner peripheral surface 16a of the connection device 16 is fitted to the outer peripheral surface of the collection port 12, and the screw portion 16ba of the outer peripheral surface 16b of the connection device 16 is screwed to and locked in the screw portion 13b formed on the inner peripheral surface of the outer peripheral wall 13. In this manner, the connection line L3 can be connected to the collection port 12.

Here. In the connection device 16 according to the present embodiment, a sealing member 17 formed from an O-ring is attached to the outer peripheral surface 16b. In a state where the connection device 16 is connected to the collection port 12, as illustrated in FIG. 9, the sealing member 17 can come into contact with and seal the inner peripheral surface 13d of the outer peripheral wall 13. In this manner, in the state where the connection device 16 is connected to the collection port 12, it is possible to block the liquid not to flow out via the discharge route β.

According to the present embodiment, in the state where the connection device 16 is connected to the collection port 12, the liquid is blocked so as not to flow out via the discharge route β. Therefore, when collecting the liquid from the collection port 12 via the connection device 16, it is possible to reliably avoid a case where the liquid leaks out from the discharge route β, and thus it is possible to more excellently circulate the collected liquid with respect to the connection line L3. In addition, similar to the first embodiment, a configuration is not required where the pressure difference forming device 14 and the collection port 12 are moved during a process where the connection device 16 is connected to the collection port 12. Therefore, it is possible to further simplify the configuration of the dialysate extraction device 9.

Next, a dialysate extraction apparatus according to a third embodiment of the present invention will be described.

Figure 10:
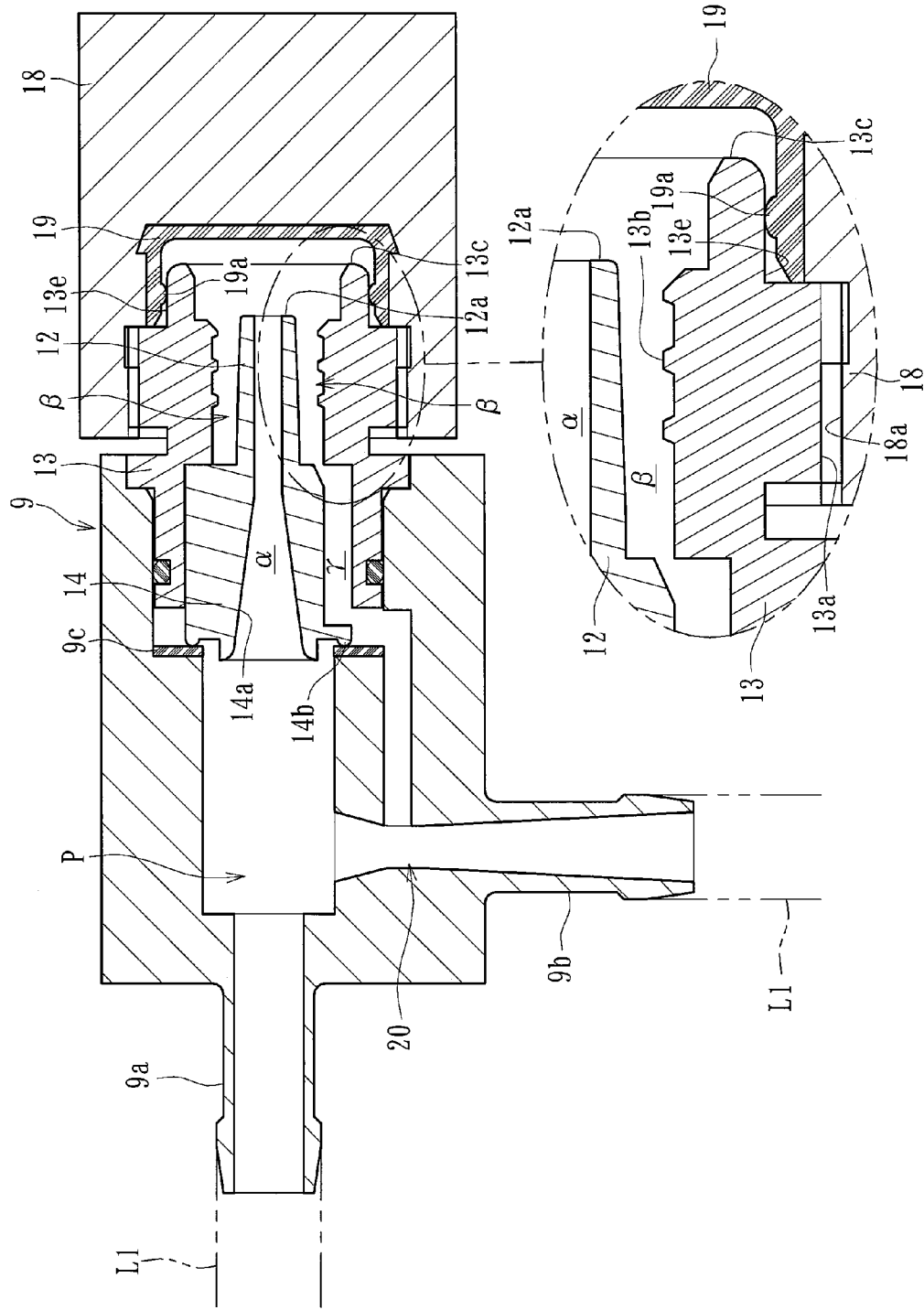
FIG. 10 is a schematic cross-sectional view of a dialysate extraction apparatus (state where an on-off device is attached to a collection port) according to a third embodiment of the present invention.

Similar to the first embodiment, the dialysate extraction apparatus according to the present embodiment is connected to the dialysate introduction line L1 of the blood purification apparatus as illustrated in FIG. 1. As illustrated in FIG. 10, the dialysate extraction apparatus includes the dialysate extraction device 9 having the inlet 9a and the outlet 9b which are connected to the dialysate introduction line L1 (flow route of a liquid) and which can circulate the liquid (dialysate) and has the collection port 12 which can collect the circulating liquid; a cap 18 serving as the on-off device which is attachable to and detachable from the collection port 12 of the dialysate extraction device 9 and which can turn on and off the collection port 12; and a venturi shape 20 as a pressure difference forming device. The same reference numerals are given to the configuring parts which are the same as those of the first embodiment, and detailed description thereof will not be repeated.

The cap 18 is attachable to and detachable from the collection port 12 of the dialysate extraction device 9, can turn on and off the collection port 12, and includes a sealing device 19 which seals between the cap and the outer peripheral surface 13e of the outer peripheral wall 13. More specifically, a sealing portion 19a which is cap-shaped along a shape of a tip side of the outer peripheral wall 13 and can come into contact with an outer peripheral surface 13e of the outer peripheral wall surface 13 is formed to protrude inward in the sealing device 19.

If the cap 18 is attached to the outer peripheral wall 13 by screwing a screw portion 18a formed on an inner peripheral surface of the cap 18 to the screw portion 13a of the outer peripheral wall 13, the sealing portion 19a can come into contact with and seal the outer peripheral surface 13e of the outer peripheral wall 13. In a state where the cap 18 is attached, in the collection port 12, the sealing portion 19a can define the guide route α which guides the liquid introduced from the inlet 9a to the tip 12a side of the collection port 12; and the discharge route β which discharges the liquid guided by the guide route α to the outlet 9b side.

According to the present embodiment, similar to the first embodiment, the dialysate extraction device 9 has the cylindrical outer peripheral wall 13 which covers the outer periphery of the collection port 12, and the cap 18 includes the sealing device 19 which seals between the cap 18 and the outer peripheral surface 13e of the outer peripheral wall 13. Therefore, in a state where the cap 18 is attached to the collection port 12, it is possible to more reliably define the guide route α and the discharge route β, and thus it is possible to more excellently circulate the cleaning water or the disinfecting solution. In particular, according to the present embodiment, the sealing device 19 seals between the cap 18 and the outer peripheral surface 13e of the outer peripheral wall 13. Accordingly, when circulating the cleaning water or the disinfecting solution, it is possible to successfully perform the cleaning or the disinfecting on the tip surface 13c of the outer peripheral wall 13.

Furthermore, in the present embodiment, the pressure difference forming device formed with the venturi shape 20 is formed in order to decrease a pressure by squeezing liquid flow from the inlet 9a toward the outlet 9b. The venturi shape 20 is formed at a merging portion with the connection route γ which is a portion of the flow route from the branch portion P toward the outlet 9b. The venturi shape 20 is configured to relatively increase a pressure of the liquid flowing toward the guide route α as compared to a pressure of the liquid flowing toward the outlet 9b, out of the liquids introduced from the inlet 9a.

According to the present embodiment, the pressure difference forming device is formed with the venturi shape 20 for decreasing the pressure by squeezing the liquid flow from the inlet 9a toward the outlet 9b. Therefore, it is possible to relatively decrease the pressure of the liquid flowing from the inlet 9a toward the outlet 9b as compared to the pressure of the liquid flowing from the inlet 9a toward the collection port 12, and thus, it is possible to reliably circulate the cleaning water or the disinfecting solution with respect to the guide route α and the discharge route β.

Next, a dialysate extraction apparatus according to a fourth embodiment of the present invention will be described.

Figure 11:
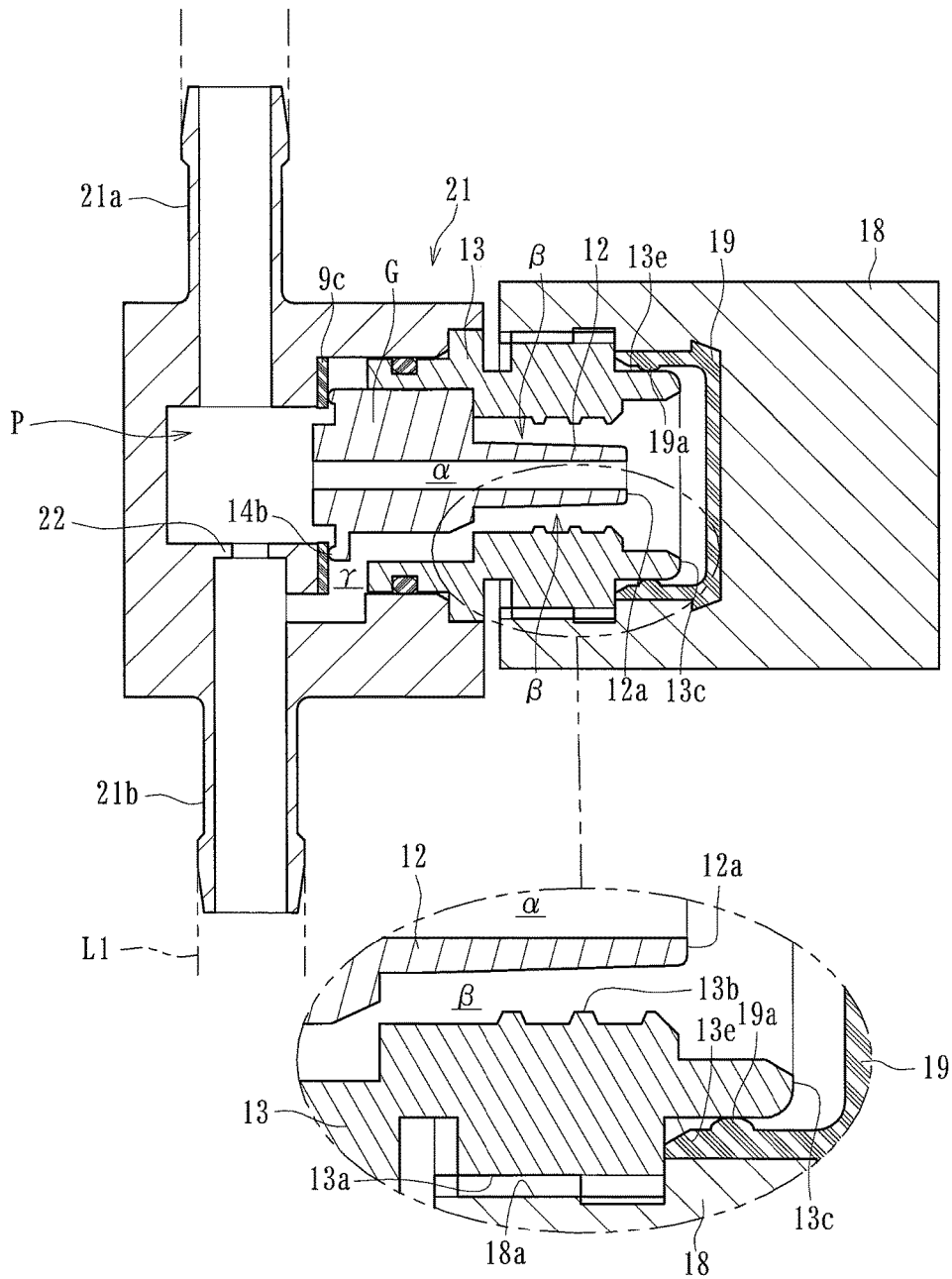
FIG. 11 is a schematic cross-sectional view of a dialysate extraction apparatus (state where an on-off device is attached to a collection port) according to a fourth embodiment of the present invention.

Similar to the first embodiment, the dialysate extraction apparatus according to the present embodiment is connected to the dialysate introduction line L1 of the blood purification apparatus as illustrated in FIG. 1. As illustrated in FIG. 11, the dialysate extraction apparatus includes a dialysate extraction device 21 having an inlet 21a and an outlet 21b which are connected to the dialysate introduction line L1 (flow route of a liquid) and which can circulate the liquid (dialysate) and having the collection port 12 which can collect the circulating liquid; the cap 18 serving as the on-off device which is attachable to and detachable from the collection port 12 of the dialysate extraction device 21 and which can turn on and off the collection port 12; and an orifice 22 as a pressure difference forming device. The same reference numerals are given to the configuring parts which are the same as those of the previous embodiment, and detailed description thereof will not be repeated.

A guide member G is arranged in the collection port 12 side near the branch portion P in the dialysate extraction device 21. The guide member G is molded integrally with the collection port 12 and a flow route leading to the guide route α is formed inside thereof. Similar to the first embodiment, the flow route inside the guide member G may have the tapered surface where a diameter thereof gradually decreases toward the collection port 12 side.

Here, in the present embodiment, there is provided a pressure difference forming device formed from the orifice 22 for decreasing the pressure by squeezing the liquid flow from the inlet 21a toward the outlet 21b. The orifice 22 is formed at a further upstream side (that is, the branch portion P side) with respect to a merging portion with the connection route γ which is a portion of the flow route from the branch portion P toward the outlet 21b. The orifice 22 is configured to relatively increase a pressure of the liquid flowing toward the guide route α as compared to a pressure of the liquid flowing toward the outlet 21b, within the liquid introduced from the Inlet 21a.

In the present embodiment, the inlet 21a and the outlet 21b are formed on substantially the same straight line, and the collection port 12 is formed at a position oriented by substantially 90 degrees with respect to a flow route configured to have the inlet 21a and the outlet 21b. However, similar to the first embodiment, the inlet 21a and the collection port 12 may be formed on substantially the same straight line in the dialysate extraction device 21. In addition, the guide member G and the collection port 12 may be used as separate parts.

According to the present embodiment, the pressure difference forming device is formed from the orifice 22 for decreasing the pressure by squeezing the liquid flow from the inlet 21a toward the outlet 21b. Therefore, it is possible to provide a pressure difference between the guide route α and the discharge route β, and thus, it is possible to reliably circulate the cleaning water or the disinfecting solution with respect to the guide route α and the discharge route β.

Next, a dialysate extraction apparatus according to a fifth embodiment of the present invention will be described.

Figure 12:
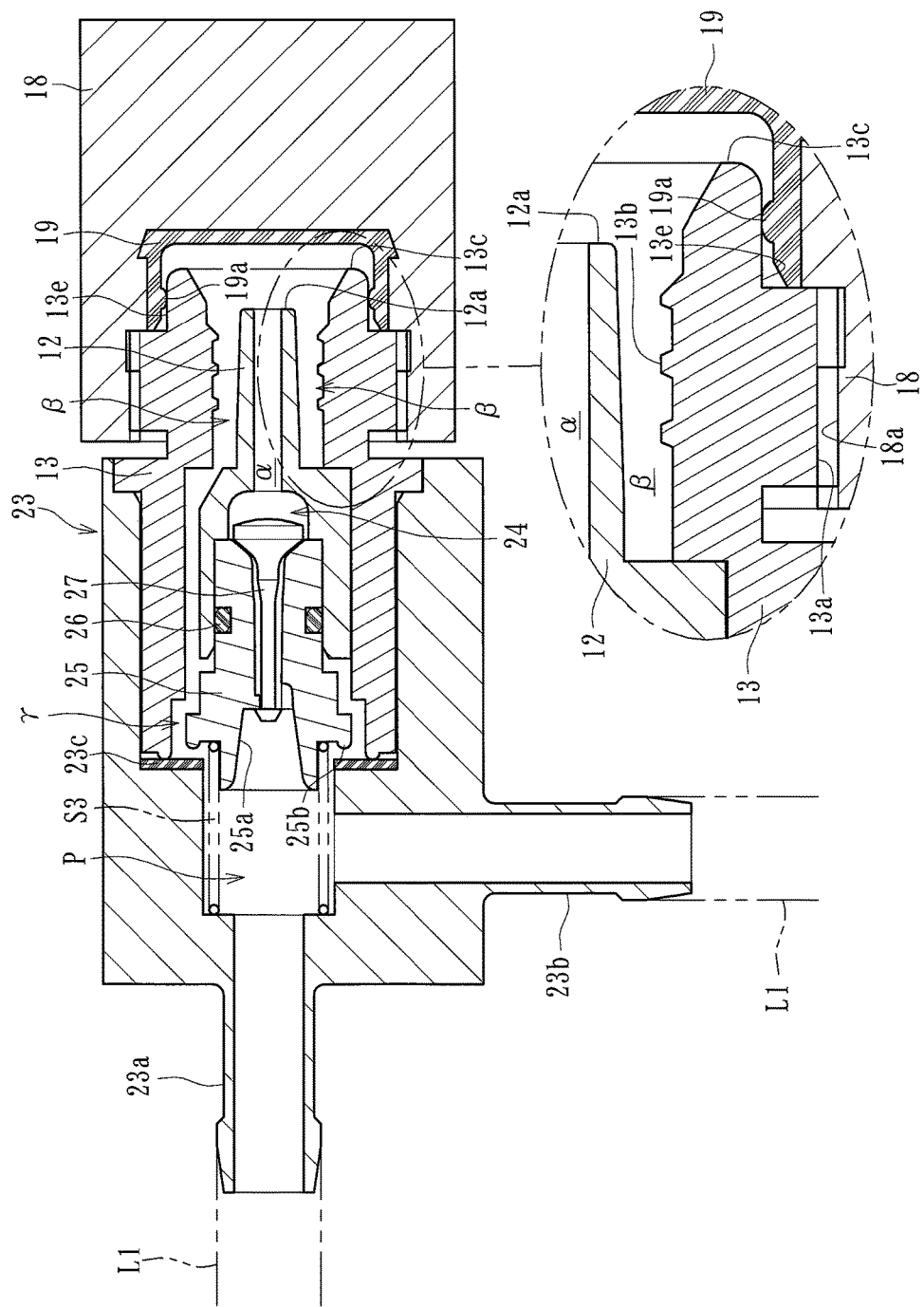
FIG. 12 is a schematic cross-sectional view of a dialysate extraction apparatus (state where an on-off device is attached to a collection port) according to a fifth embodiment of the present invention.
Figure 13:
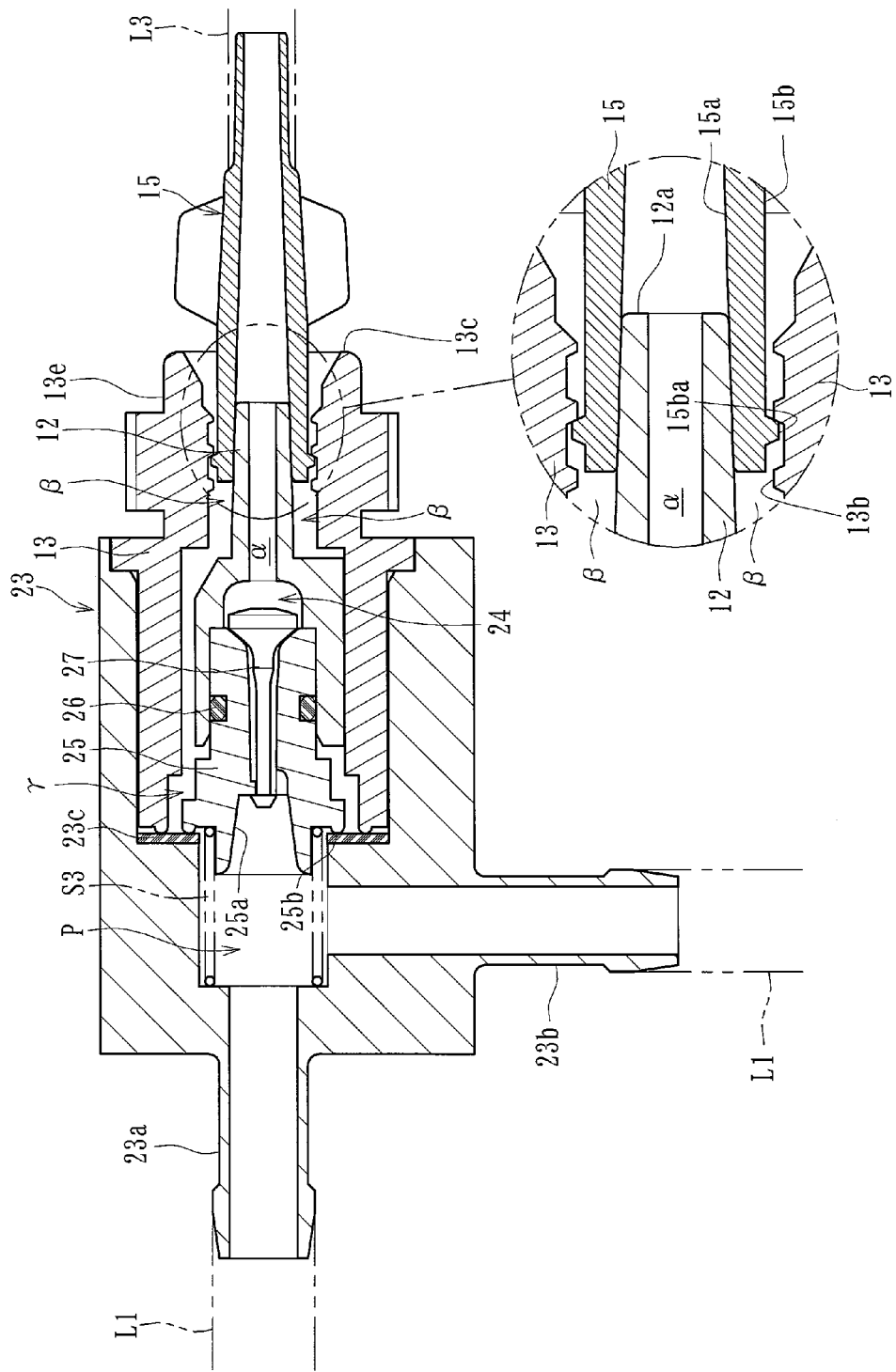
FIG. 13 is a schematic cross-sectional view illustrating a dialysate extraction device (state where an on-off device is detached and state where a connection device is connected) in the dialysate extraction apparatus.

Similar to the first embodiment, the dialysate extraction apparatus according to the present embodiment is connected to the dialysate introduction line L1 of the blood purification apparatus as illustrated in FIG. 1. As illustrated in FIGS. 12 and 13, the dialysate extraction apparatus includes a dialysate extraction device 23 having an inlet 23a and an outlet 23b which are connected to the dialysate introduction line L1 (flow route of a liquid) and which can circulate the liquid (dialysate) and having the collection port 12 which can collect the circulating liquid; the cap 18 serving as the on-off device which is attachable to and detachable from the collection port 12 of the dialysate extraction device 23 and which can turn on and off the collection port 12; and a pressure difference forming device 25 as a pressure difference forming device. The same reference numerals are given to the configuring parts which are the same as those of the first embodiment, and detailed description thereof will not be repeated.

Similar to the first embodiment, the pressure difference forming device 25 according to the present embodiment is arranged near the branch portion P of the dialysate extraction device 23, and is formed to have a circulation route 25a of the liquid flowing from the inlet 23a toward the collection port 12. The circulation route 25a has a tapered surface where a diameter of the flow route gradually decreases toward the collection port 12 side (right side in FIG. 12). After being formed to be separate from the collection port 12, the pressure difference forming device 25 is connected to the collection port 12. A sealing device 26 seals a connection portion between the pressure difference forming device 25 and the collection port 12.

A to-be-sealed portion 25b is formed in a portion opposing a sealing member 23c in the pressure difference forming device 25. The pressure difference forming device 25 and the collection port 12 are always biased in a direction in which the to-be-sealed portion 25b is separated from the sealing member 23c by a spring S3. Then, when the connection device 15 is connected to the collection port 12 (that is, during a process where the screw portion 15ba of the outer peripheral surface 15b of the connection device 15 is screwed to the screw portion 13b formed on the inner peripheral surface of the outer peripheral wall 13), as illustrated in FIG. 13, the pressure difference forming device 25 and the collection port 12 are moved against a biasing force of the spring S3, and the to-be-sealed portion 25b comes into contact with and seals the sealing member 23c, thereby enabling the connection route γ to be blocked.

In a state where the connection device 15 is connected to the collection port 12, the liquid is blocked so as not to flow out via the discharge route β. In this manner, in the state where the connection device 15 is connected to the collection port 12, the liquid is blocked so as not to flow out via the discharge route β. Therefore, when collecting the liquid from the collection port 12 via the connection device 15. It is possible to reliably avoid a case where the liquid leaks out from the discharge route β, and thus, it is possible to more excellently circulate the collected liquid with respect to the connection line L3.

Here, the dialysate extraction device 23 according to the present embodiment includes a check valve 27. The check valve 27 is arranged in a flow route 24 in the connection portion between the pressure difference forming device 25 and the collection port 12, allows the liquid to flow out from the collection port 12, and blocks the liquid not to flow in from outside via the collection port 12. The check valve 27 allows the liquid to flow from a flow route 25a toward the guide route α and regulates the liquid not to flow from the guide route α toward the flow route 25a. Therefore, when the connection line L3 is connected to the collection port 12 via the connection device 15, the collection of the liquid can be excellently maintained, and thus, it is possible to avoid a case where the liquid inside the connection line L3 flows in through the collection port 12.

Next, a dialysate extraction apparatus according to a sixth embodiment of the present invention will be described.

Figure 14:
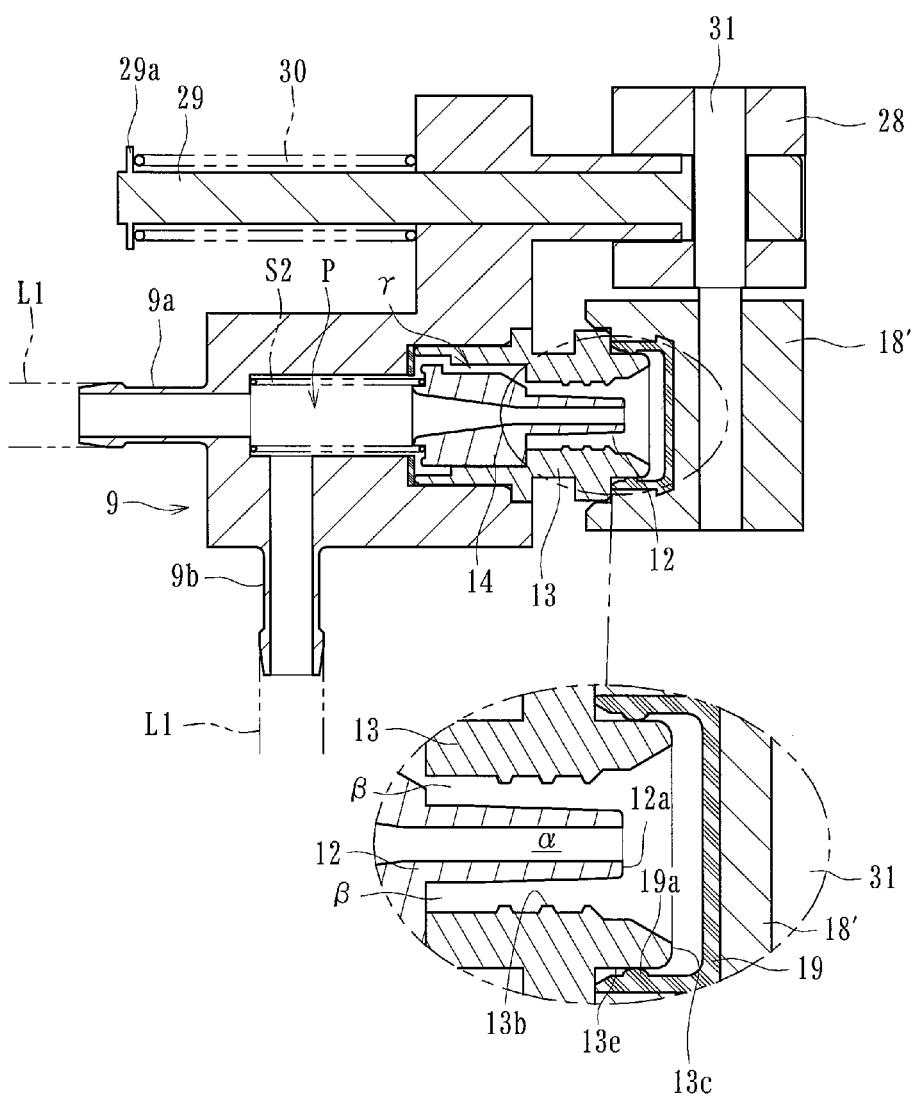
FIG. 14 is a schematic cross-sectional view of a dialysate extraction apparatus (state where an on-off device is attached to a collection port) according to a sixth embodiment of the present invention.
Figure 15:
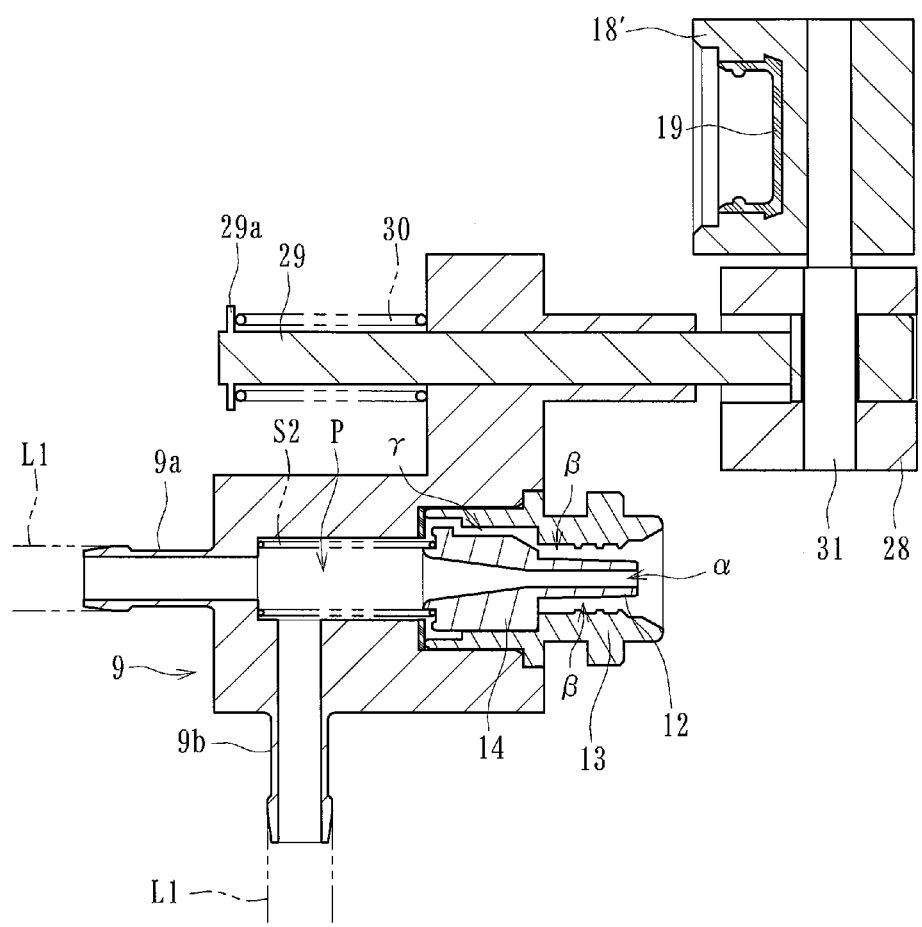
FIG. 15 is a schematic cross-sectional view illustrating a state where an on-off device is detached from a collection port of the dialysate extraction apparatus and then is rotated about a shaft member 29.
Figure 16:
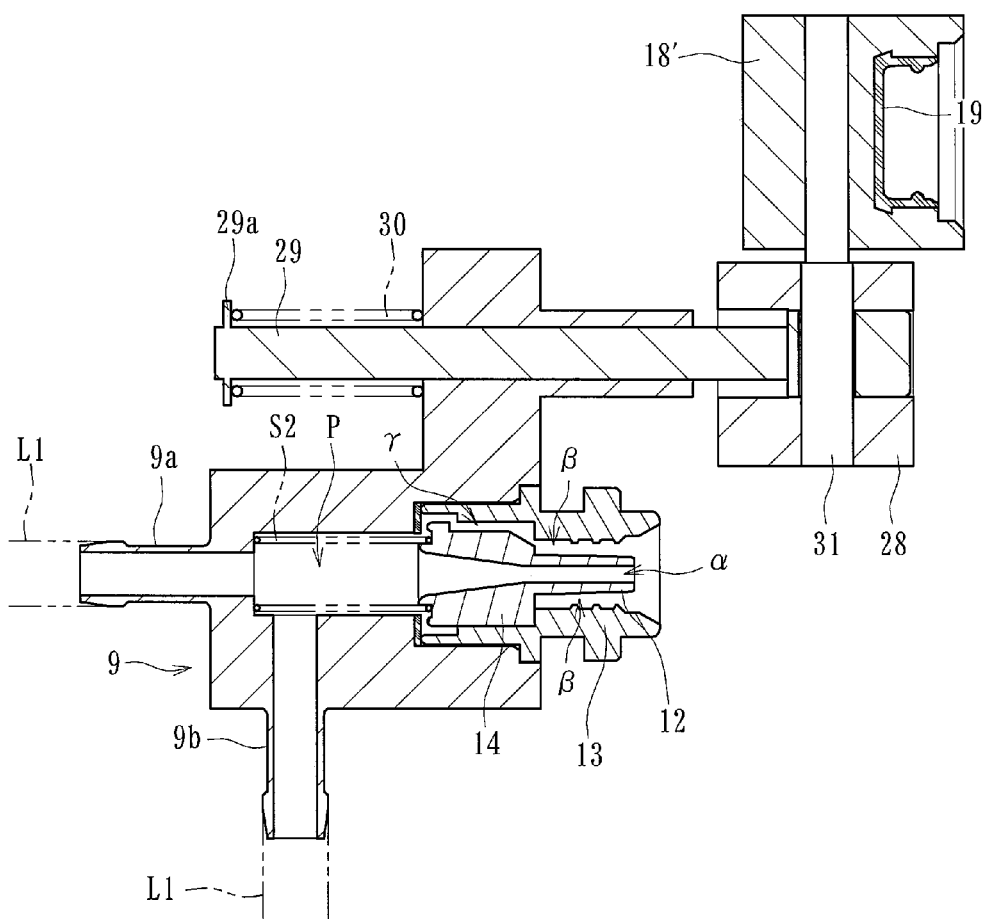
FIG. 16 is a schematic cross-sectional view illustrating a state where an on-off device is detached from a collection port of the dialysate extraction apparatus, is rotated about a shaft member 29, and is rotated about a shaft member 31.

Similar to the first embodiment, the dialysate extraction apparatus according to the present embodiment is connected to the dialysate introduction line L1 of the blood purification apparatus as illustrated in FIG. 1. As illustrated in FIGS. 14 to 16, the dialysate extraction apparatus includes the dialysate extraction device 9; a cap 18' serving as the on-off device which is attachable to and detachable from the collection port 12 of the dialysate extraction device 9 and which can turn on and off the collection port 12; and a holding device 28 which can hold a closed state of the cap 18'. The dialysate extraction device 9 adopted in the present embodiment has the configuration the same as that of the first embodiment (however, the screw portion 13a of the outer peripheral wall 13 is not formed). Therefore, detailed description thereof will not be repeated.

As illustrated in FIG. 14, the holding device 28 is configured to have a shaft member 29, a spring 30 and a shaft member 31, and is rotatable around the shaft member 29. In addition, a spring bearing 29a is formed in a base end of the shaft member 29. The spring 30 is interposed between the spring bearing 29a and the dialysate extraction device 9. In this manner, the holding device 28 is always biased in the leftward direction in FIG. 14 by a biasing force of the spring 30.

The cap 18' is supported in a tip of the shaft member 31 and is rotatable around the shaft member 31. That is, the cap 18' is rotatable around the shaft member 29 and is rotatable around the shaft member 31. In addition, the sealing device 19 similar to that of the third embodiment is attached to the cap 18' in order to seal between the cap 18' and the outer peripheral surface of the outer peripheral wall 13. In contrast, the screw portion 18a as in the third embodiment is not formed (screw portion 13a of the outer peripheral wall 13 is also not formed likewise).

In a state where the cap 18' covers the collection port 12 (refer to FIG. 14), the cap 18' is pressed against the outer peripheral wall 13 (collection port 12 side) by the biasing force of the spring 30 so as to maintain a closed state. In addition, if the holding device 28 together with the cap 18' is moved against the biasing force of the spring 30 (moved in the rightward direction in FIG. 14), the cap 18' is separated from the outer peripheral wall 13. In this state, if the cap 18's further rotated around the shaft member 29, as illustrated in FIG. 15, the collection port 12 can be left in an opened state. In this manner, it is possible to connect the connection device 15 to the collection port 12 (refer to FIG. 5). If the cap 18' is rotated around the shaft member 31 from the state in FIG. 15, as illustrated in FIG. 16, an orientation of the cap 18' is reversed. In this state, it is possible to easily replace the sealing device 19 or perform maintenance work.

According to the present embodiment, the sealing of the outer peripheral wall 13 using the cap 18' can be firmly and reliably performed. When the collection port 12 is in the opened state, it is possible to avoid a case where the cap 18' is lost. In addition, if a detection device is disposed in order to detect the orientation of the holding device 28 (position rotating around the shaft member 29), it is possible to detect whether the collection port 12 is in the opened state or the closed state. The dialysate extraction device according to the present embodiment is the same as that of the first embodiment, but may be configured to have any form.

Next, a dialysate extraction apparatus according to a seventh embodiment of the present invention will be described.

Figure 17:
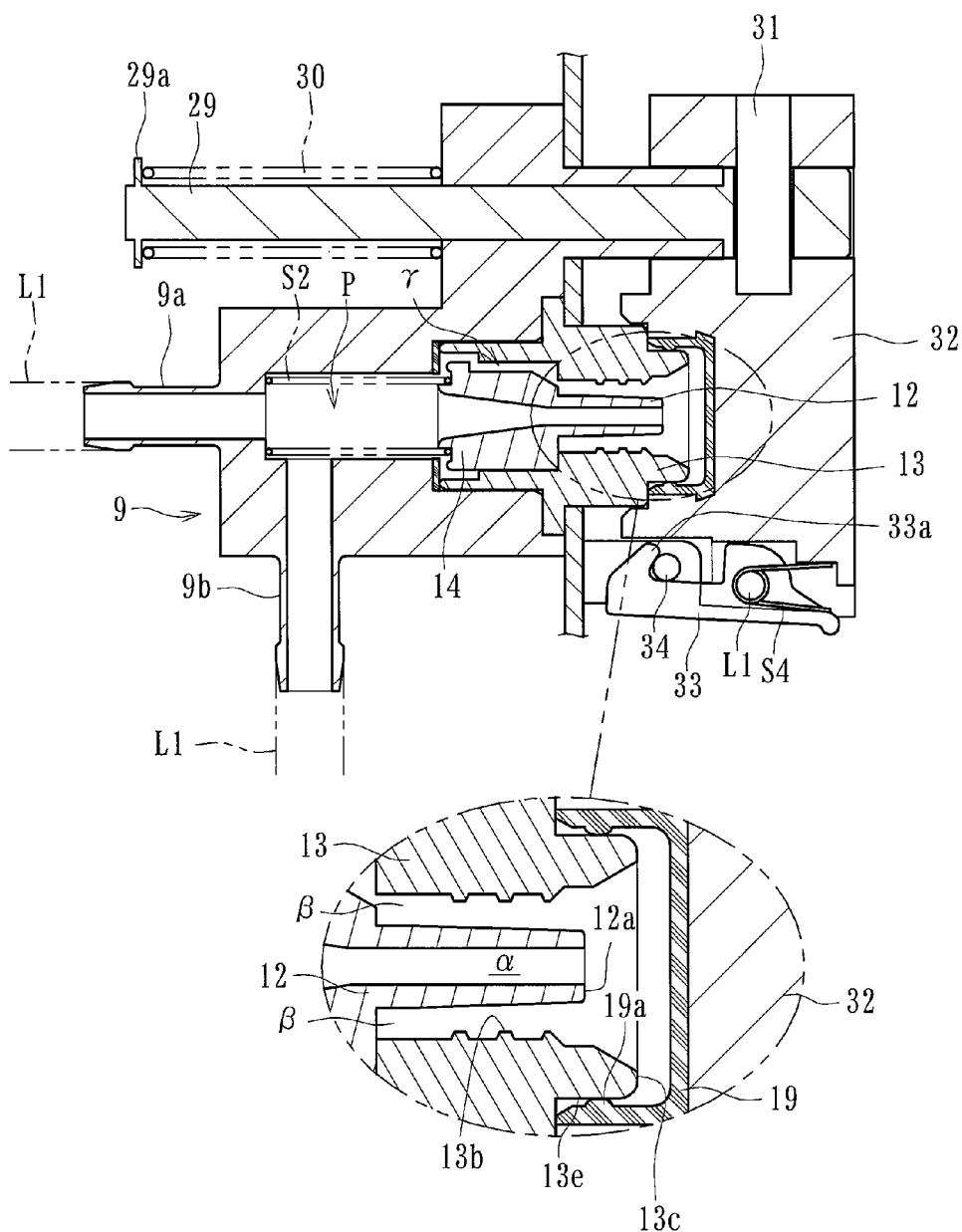
FIG. 17 is a schematic cross-sectional view of a dialysate extraction apparatus (state where an on-off device is attached to a collection port) according to a seventh embodiment of the present invention.
Figure 18:
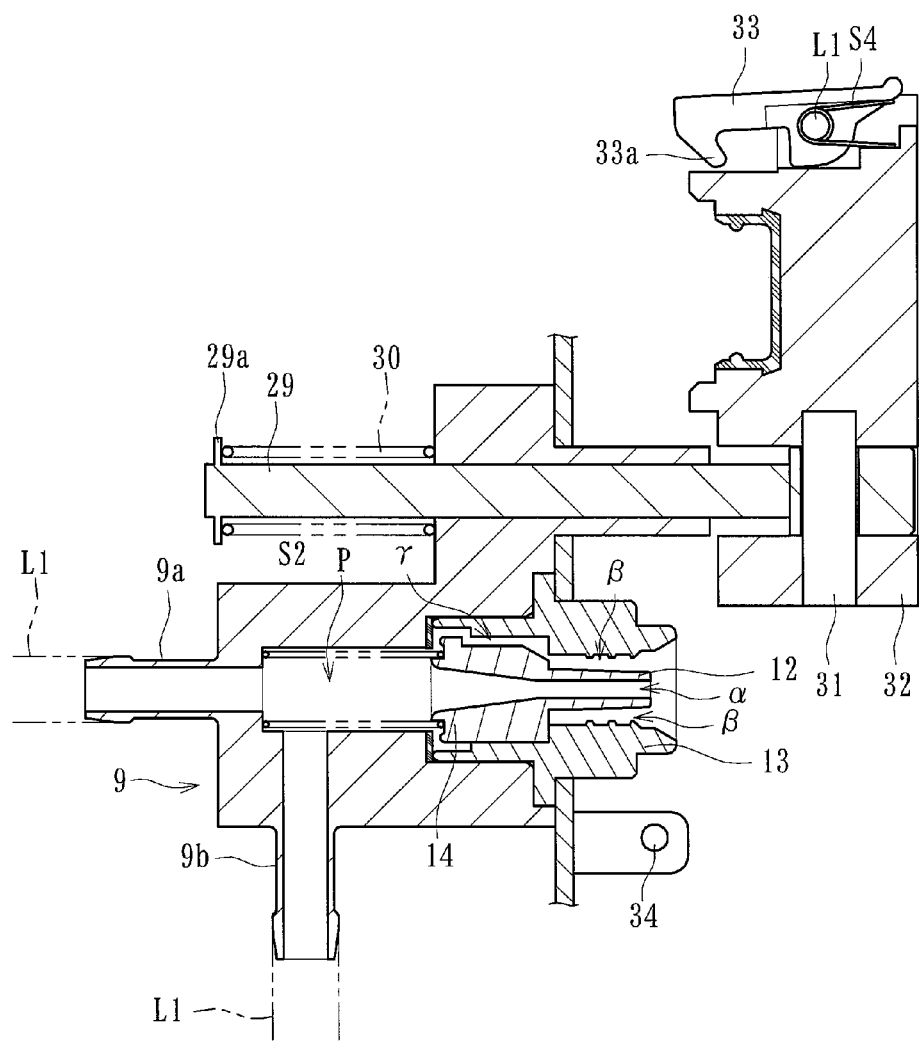
FIG. 18 is a schematic cross-sectional view illustrating a state where an on-off device is detached from a collection port of the dialysate extraction apparatus and then is rotated about a shaft member 29.

Similar to the first embodiment, the dialysate extraction apparatus according to the present embodiment is connected to the dialysate introduction line L1 of the blood purification apparatus as illustrated in FIG. 1. As illustrated in FIGS. 17 to 18, the dialysate extraction apparatus includes the dialysate extraction device 9; a cap 32 serving as the on-off device which is attachable to and detachable from the collection port 12 of the dialysate extraction device 9 and which can turn on and off the collection port 12; and a locking device 33 which can hold a closed state of the cap 32. The dialysate extraction device 9 adopted in the present embodiment has the configuration the same as that of the first embodiment (however, the screw portion 13a of the outer peripheral wall 13 is not formed). Therefore, detailed description thereof will not be repeated.

As illustrated in FIG. 17, the cap 32 is configured to have the shaft member 29, the spring 30 and the shaft member 31, and is rotatable around the shaft member 29. In addition, the spring bearing 29a is formed in the base end of the shaft member 29. The spring 30 is interposed between the spring bearing 29a and the dialysate extraction device 9. In this manner, the cap 32 is always biased in the leftward direction in FIG. 17 by the biasing force of the spring 30.

Furthermore, the cap 32 is supported in the tip of the shaft member 31 and is rotatable around the shaft member 31. That is, the cap 32 is rotatable around the shaft member 29 and is rotatable around the shaft member 31. In addition, the sealing device 19 similar to that of the third embodiment is attached to the cap 32 in order to seal between the cap 32 and the outer peripheral surface of the outer peripheral wall 13. In contrast, the screw portion 18a as in the third embodiment is not formed (screw portion 13a of the outer peripheral wall 13 is also not formed likewise).

Furthermore, the locking device 33 formed in the cap 32 has a locking pawl 33a in a tip thereof and is rotatable around a rocking shaft L1. The locking device 33 is configured to be capable of holding the closed state of the cap 32 by locking the locking pawl 33a in a rod-shaped locked portion 34 which is formed in a fixing side. The locking device 33 is always biased in a direction where the locking pawl 33a is locked in the locked portion 34 by a spring S4.

In a state where the cap 32 covers the collection port 12 (refer to FIG. 17), the locking pawl 33a is locked in the locked portion 34, and the cap 32 is pressed against the outer peripheral wall 13 (collection port 12 side) by the biasing force of the spring 30 so as to maintain a closed state. In addition, if the locking device 33 is rocked against the biasing force of the spring S4, the locking is released in the locked portion 34 using the locking pawl 33a and then the cap 32 is moved against the biasing force of the spring 30 (moved in the rightward direction in FIG. 14), the cap 32 being separated from the outer peripheral wall 13. In this state, if the cap 32 is further rotated around the shaft member 29, as illustrated in FIG. 18, the collection port 12 can be left in the opened state. In this manner, it is possible to connect the connection device 15 to the collection port 12 (refer to FIG. 5). If the cap 32 is rotated around the shaft member 31 from the state in FIG. 18, an orientation of the cap 32 is reversed as in the sixth embodiment. In this state, it is possible to easily replace the sealing device 19 or perform maintenance work.

According to the present embodiment, the sealing of the outer peripheral wall 13 using the cap 32 can be firmly and reliably performed. When the collection port 12 is in the opened state, it is possible to avoid a case where the cap 32 is lost. In addition, the locking device 33 can firmly hold the closed state of the cap 32. Accordingly, it is possible to avoid a case where the cap 32 is unintentionally rocked due to vibrations and the collection port 12 is opened. Further, similar to the sixth embodiment, if a detection device is disposed in order to detect the orientation of the holding device 28 (position rotating around the shaft member 29), it is possible to detect whether the collection port 12 is in the opened state or the closed state. The dialysate extraction device according to the present embodiment is the same as that of the first embodiment, but may be configured to have any form.

According to the above-described first to seventh embodiments, the cleaning water or the disinfecting solution can be circulated via the guide route and the discharge route. Therefore, it is possible to provide the blood purification apparatus (hemodialysis apparatus) which can reliably perform the cleaning and the disinfecting in the inside of the collection port without extending a separate flow route from the on-off device. Furthermore, in addition to the function of collecting the liquid, the collection port also has the function of defining the guide route and the discharge route. Therefore, it is possible to provide the blood purification apparatus (hemodialysis apparatus) in which the configuration can be simplified by eliminating the need to provide the separate defining device.

Hitherto, the present embodiments have been described, but the present invention is not limited thereto. For example, the present invention may not include the pressure difference forming device or may not include the check valve. In addition, in a state where the on-off device such as the cap is attached, as long as the present invention includes the collection port 12 which defines the guide route α for guiding the liquid introduced from the inlet to the tip 12a side of the collection port 12; and the discharge route β for discharging the liquid guided by the guide route α to the outlet side, the present invention may not include the outer peripheral wall 13.

Further, the blood purification apparatus which adopts the present embodiments may have any form. For example, those which introduce the dialysate to a chamber or discharge the dialysate from the chamber may be used instead of the duplex pump 7, or those which include other forms of the blood purifier instead of the dialyzer 1 may be used. Furthermore, in the present embodiments, any dialysate extraction apparatus is arranged in the dialysate introduction line L1 of the dialysis device, but may be arranged in other flow routes inside the dialysis device.

In a state where an on-off device is attached, as long as there is provided a dialysate extraction apparatus including a collection port which defines a guide route for guiding a liquid introduced from an inlet to a tip side of the collection port; and a discharge route for discharging the liquid guided by the guide route to an outlet side, the dialysate extraction apparatus can be applied to those which have different outer shapes or other additional functions.

REFERENCE SIGN UST 1 dialyzer (blood purifier)
2 artery side blood circuit
3 vein side blood circuit
4 blood pump
5 artery side air trap chamber
6 vein side air trap chamber
7 duplex pump
8 ultraflitration pump
9 dialysate extraction device
10 cap (on-off device)
11 sealing device
12 collection port
13 outer peripheral wall
14 pressure difference forming device
15 connection device
16 connection device
17 sealing member
18, 18' cap
19 sealing device
20 venturi shape
21 dialysate extraction device
22 orifice
23 dialysate extraction device
24 flow route
25 pressure difference forming device
26 sealing device
27 check valve
28 holding device
29 shaft member
30 spring
31 shaft member
32 cap
33 locking device
34 locked portion

The invention claimed is:

1. A dialysate extraction apparatus comprising:
a dialysate extraction device having an inlet and an outlet which are connected to a flow route of a liquid and which circulates the liquid, and having a collection port which collects the liquid that is circulated; and
an on-off device which is attachable to and detachable from the collection port of the dialysate extraction device and which turns on and off the collection port,
wherein in a state where the on-off device is attached, the collection port defines a guide route which guides the liquid introduced from the inlet to a tip side of the collection port, and a discharge route which discharges the liquid guided by the guide route back through the collection port to the outlet;
wherein the dialysate extraction device has a cylindrical outer peripheral wall which covers an outer periphery of the collection port, and
wherein the on-off device includes a sealing device which seals between the on-off device and an outer peripheral surface of the outer peripheral wall or between the on-off device and a tip surface of the outer peripheral wall; and
wherein the collection port is connected to a connection line for circulating an extracted liquid via a connection device, and
wherein the connection line is connected to the collection port by fitting an inner peripheral surface of the connection device into the outer peripheral surface of the collection port and by engaging an outer peripheral surface of the connection device with an inner peripheral surface of the outer peripheral wall.

2. The dialysate extraction apparatus according to claim 1, wherein inside of the collection port serves as the guide route, and
wherein a section between an outer peripheral surface of the collection port and an inner peripheral surface of the outer peripheral wall serves as the discharge route.

3. The dialysate extraction apparatus according to claim 1, wherein the outer peripheral wall is formed to protrude by covering a tip of the collection port.

4. The dialysate extraction apparatus according to claim 1, wherein in a state where the connection device is connected to the collection port, the liquid is blocked so as not to flow out via the discharge route.

5. The dialysate extraction apparatus according to claim 4, wherein the dialysate extraction device includes a pressure difference forming device which increases a pressure of a liquid flowing toward the guide route as compared to a pressure of a liquid flowing toward the outlet out of the liquid introduced from the inlet.

6. The dialysate extraction apparatus according to claim 1, wherein the dialysate extraction device includes a pressure difference forming device which increases a pressure of a liquid flowing toward the guide route as compared to a pressure of a liquid flowing toward the outlet out of the liquid introduced from the inlet.

7. The dialysate extraction apparatus according to claim 6, wherein the pressure difference forming device and the collection port are formed from an integral part.

8. The dialysate extraction apparatus according to claim 7, wherein the pressure difference forming device is formed to have a circulation route of the liquid flowing from the inlet toward the collection port, and
wherein the circulation route has a tapered surface in which a diameter of the flow route gradually decreases toward the collection port; and
wherein another pressure difference forming device is formed to have an orifice or a venturi shape for decreasing a pressure by squeezing liquid flow from the inlet toward the outlet.

9. The dialysate extraction apparatus according to claim 6, wherein the pressure difference forming device is formed to have a circulation route of the liquid flowing from the inlet toward the collection port, and
wherein the circulation route has a tapered surface in which a diameter of the flow route gradually decreases toward the collection port.

10. The dialysate extraction apparatus according to claim 6, wherein the pressure difference forming device has an orifice or a venturi shape for decreasing a pressure by squeezing liquid flow from the inlet toward the outlet and wherein the pressure forming device is upstream or at a merging portion of a connection flow route of the outlet and a branch portion connected to the inlet, the outlet and the collection port.

11. The dialysate extraction apparatus according to claim 10, wherein the dialysate extraction device includes a check valve which allows the liquid to flow out from the collection port and blocks the liquid not to flow in from outside via the collection port.

12. The dialysate extraction apparatus according to claim 1, wherein the dialysate extraction device includes a check valve which allows the liquid to flow out from the collection port and blocks the liquid not to flow in from outside via the collection port.

13. The dialysate extraction apparatus according to claim 1, wherein the inlet and the collection port are formed on a substantially the same straight line.

14. A blood purification apparatus comprising:
the dialysate extraction apparatus according to claim 1.

15. The dialysate extraction apparatus according to claim 1, wherein inside of the collection port serves as the guide route, and
wherein a section between an outer peripheral surface of the collection port and an inner peripheral surface of the outer peripheral wall serves as the discharge route; and
wherein the outer peripheral wall is formed to protrude by covering a tip of the collection port.

16. The dialysate extraction apparatus according to claim 1, wherein the dialysate extraction device includes a branch portion connected to the inlet, the outlet and the collection port so that the liquid can flow from the inlet to through the branch portion to either the collection port or the outlet.

17. The dialysate extraction apparatus according to claim 16, wherein the dialysate extraction device includes a connection route so that fluid exiting the collection port is circulated back into the branch portion when the on-off device is attached.

* * * * *